US008067440B2

(12) United States Patent
Charette et al.

(10) Patent No.: US 8,067,440 B2
(45) Date of Patent: Nov. 29, 2011

(54) PHOSPHONIUM SALTS DERIVATIVES AND USES THEREOF

(75) Inventors: Andre Charette, Longueuil (CA); Jean-Christophe Poupon, Coulombes (FR); Alessandro Boezio, Somerville, MA (US)

(73) Assignee: Valorisation-Recherche, Limited Partnership, Montreal (CA)

( * ) Notice: Subject to any disclaimer, the term of this patent is extended or adjusted under 35 U.S.C. 154(b) by 0 days.

(21) Appl. No.: 12/974,821

(22) Filed: Dec. 21, 2010

(65) Prior Publication Data

US 2011/0092683 A1 Apr. 21, 2011

Related U.S. Application Data

(60) Division of application No. 11/539,075, filed on Oct. 5, 2006, now Pat. No. 7,880,037, which is a continuation-in-part of application No. PCT/CA2005/000523, filed on Apr. 6, 2005.

(60) Provisional application No. 60/560,592, filed on Apr. 9, 2004.

(51) Int. Cl.
*A61K 31/44* (2006.01)

(52) U.S. Cl. .......................................... 514/332

(58) Field of Classification Search .................. 514/332
See application file for complete search history.

(56) References Cited

U.S. PATENT DOCUMENTS 5,445,724 A 8/1995 Burkhart (Continued)

FOREIGN PATENT DOCUMENTS

CA 2 311 318 A1 6/1999

(Continued)

OTHER PUBLICATIONS

Charette, A.B., et al., "New Solubility Controlling Group for Solution Phase Chemistry," UCI-Merck Symposium, Irvine, Calif., Sep. 17,2005, pp. 27-54.

(Continued)

*Primary Examiner* — Taofiq A Solola

(74) *Attorney, Agent, or Firm* — Christensen O'Connor Johnson Kindness PLLC

(57) ABSTRACT

There are provided compounds of formulas (VA), (VIA), (VIIA) (IXA), (XIA), (XIIA), (XIIIA), and (XIVA):

(VA)

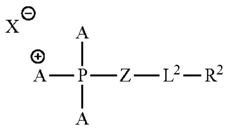

-continued (VIA)

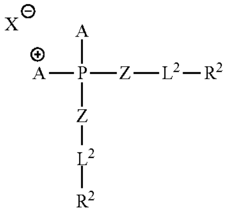

(VIIA)

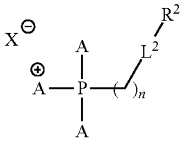

(IXA)

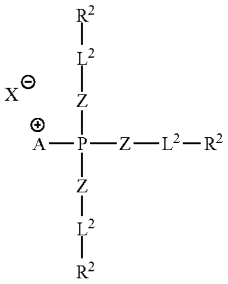

(XIVA)

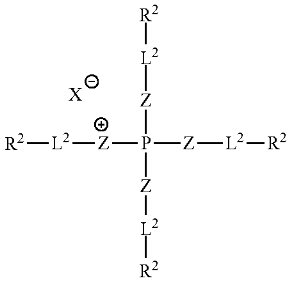

(XIA)

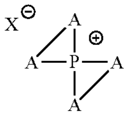

(XIIA)

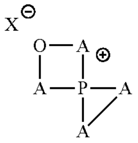

(XIIIA)

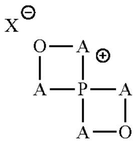

wherein A, Z, $R^2$, $X^-$, and $L^2$ represent various different possibilities. Methods for using such compounds are also provided.

19 Claims, No Drawings

U.S. PATENT DOCUMENTS

| | | | |
|---|---|---|---|
| 5,714,360 | A | 2/1998 | Swan |
| 6,267,913 | B1 | 7/2001 | Marder |

FOREIGN PATENT DOCUMENTS

| | | | |
|---|---|---|---|
| CA | 2 481 202 | A1 | 10/2003 |
| CA | 2 494 173 | A1 | 2/2004 |
| CN | 1247870 | A | 3/2000 |
| DE | 19914193 | A1 | 9/2000 |
| EP | 0 296 550 | A2 | 12/1988 |
| EP | 1 388 552 | A1 | 2/2004 |
| JP | 7330762 | A | 12/1995 |
| JP | 2002-069110 | A | 3/2002 |
| JP | 2002-338587 | A | 11/2002 |
| WO | 88/07537 | A1 | 10/1988 |
| WO | 2005/035546 | A1 | 4/2005 |

OTHER PUBLICATIONS

Charette, A.B., et al., "Synthesis of a Triphenylphosphine Reagent on Non Cross-Linked Polystyrene Support: Application to the Staudinger/Aza-Wittig Reaction," Organic Letters 2(24):3777-3779, Nov. 2000.

Corey, E.J., and P.L. Fuchs, "A Synthetic Method for Formyl→Ethynyl Conversion (RCHO→RC≡CH or RC≡CR')," Tetrahedron Letters 13(36):3769-3772, Aug. 1972.

Curran, D.P., "Strategy-Level Separations in Organic Synthesis: From Planning to Practice," Angewandte Chemie International Edition 37(9):1174-1196, May 1998.

Dickerson, T.J., et al., "Soluble Polymers as Scaffolds for Recoverable Catalysts and Reagents," Chemical Reviews 102(10):3325-3344, Oct. 2002.

Drawe, H., and G. Caspari, "Radiation-Chemical Synthesis of Phosphonium and Arsonium Salts," Angewandte Chemie International Edition 5(3):317-318, Mar. 1966.

Enholm, E.J., et al., "An Allylstannane Reagent on Non-Cross-Linked Polystyrene Support," Organic Letters 1(5):689-691, Sep. 1999.

Garber, S.B., et al., "Efficient and Recyclable Monomeric and Dendritic Ru-Based Metathesis Catalysts," Journal of the American Chemical Society 122(34):8168-8179, Aug. 2000.

Goetz, N., et al., "Charge Distribution Reactivity of Organic Phosphorus Compounds. AVII. Preparation and Phosphorus-31 NMR Data of Some P-Substituted Aromatic and Aromatic-Aliphatic Phosphonium Salts," Phosphorus and the Related Group V Elements 1(5):217-221, 1972.

Griffith, W.P., et al., "Preparation and Use of Tetra-n-butylammonium Per-Ruthenate (TBAP Reagent) and Tetra-n-propylammonium Per-Ruthenate (TPAP Reagent) as New Catalytic Oxidants for Alcohols," Journal of the Chemical Society, Chemical Communications 21:1625-1627, Nov. 1987.

Han, H., and K.D. Janda, "Soluble Polymer-Bound Ligand-Accelerated Catalysis: Asymmetric Dihydroxylation," Journal of the American Chemical Society 118(32):7632-7633, Aug. 1996.

Aldrich Chemical Company, "Aldrich: Handbook of Fine Chemicals and Laboratory Equipment," Milwaukee, Wisc., 2000-2001, pp. 265,338,693,1070, and 1695.

Bailey, A.J., et al., "Studies on Transition-Metal Oxo and Nitrido Complexes. 13. Perruthenate and Ruthenate Anions as Catalytic Organic Oxidants," Inorganic Chemistry 32:268-271, Feb. 1993.

Barrett, A.G.M., et al., "ROMPgel Reagents in Parallel Synthesis," Chemical Reviews 102(10):3301-3324, Oct. 2002.

Benaglia, M., et al., "Polymer-Supported Organic Catalysts," Chemical Reviews 103(9):3401-3429, Sep. 2003.

Bergbreiter, D.E., "Using Soluble Polymers to Recover Catalysts and Ligands," Chemical Reviews 102(10):3345-3384, Oct. 2002.

Bhalay, G., et al., "Supported Reagents: Opportunities and Limitations," Synlett 12:1846-1859, 2000.

Boulton, L.T., et al., "Synthesis of the Potent Antiglaucoma Agent, Travoprost," Organic Process Research & Development 6(2):138-145, Feb. 2002.

Brunel, J., et al., "Propeller-Shaped Octupolar Molecules Derived From Triphenylbenzene for Nonlinear Optics: Synthesis and Optical Studies," Chemistry of Materials 15(21):4139-4148, Oct. 2003.

Charette, A.B., et al., "New Solubility Controlling Group for Solution Phase Chemistry," 230th American Chemical Society National Meeting, Washington, D.C., Aug. 28-Sep. 1, 2005, pp. 1-27.

Hanawa, H., et al., "Bis(((S)-binaphthoxy(isopropoxy)titanium) Oxide as a μ-Oxo-Type Chiral Lewis Acid: Application to Catalytic Asymmetric Allylation of Aldehydes," Journal of the American Chemical Society 125(7):1708-1709, Feb. 2003.

Hassner, A., and C. Stumer, "Organic Syntheses Based on Name Reactions," 2d ed., Pergamon Press, London, 2002, pp. 249,250, and 409.

Heckel, A., and D. Seebach, "Immobilization of TADDOL With a High Degree of Loading on Porous Silica Gel and First Applications in Enantioselective Catalysis," Angewandte Chemie International Edition 39(1):163-165, Jan. 2000.

Horton, D.A., et al., "The Combinatorial Synthesis of Bicyclic Privileged Structures or Privileged Substructures," Chemical Reviews 103(3):893-930, Mar. 2003.

Ivanov, E.S., and T.K. Atanasyan, "Effect of Quaternary Phosphonium Iodide Salts on Hydrogen Embrittlement and Elasticity of Carbon Steel," Fiziko-Khimicheskaia Materialov 17(6):107-109, 1981.

Ji, B., et al "Assembled Dendritic Titanium Catalysts for Enantioselective Hetero-Diels-Alder Reaction of Aldehydes with Danishefsky's Diene," Chemistry, A European Journal 9(24):5989-5996, Dec. 2003.

Jiang, Y.-S., et al., "Electrochemical and Spectral Studies on Ferrocene Derivatives With Electron Pushing and Drawing Substituents," Gaodeng Xuexiao Huaxue Xuebao 16(Suppl. 11):241-245, 1995.

Kimura, J., et al., "Studies on Nucleosides and Nucleotides. VII. Preparation of Pyrimidine Nucleoside 5'-Phosphates and N3, 5'-Purine Cyclonucleosides by Selective Activation of the 5'-Hydroxyl Group," Bulletin of the Chemical Society of Japan 52(4):1191-1196, Apr. 1979.

Kirschning, A., et al., "Functionalized Polymers—Emerging Versatile Tools for Solution-Phase Chemistry and Automated Parallel Synthesis," Angewandte Chemie International Edition 40(4):650-679, Feb. 2001.

Kiselev, A.S., et al., "Reactions of N-Fluoropyridinium Salts With Phosphorus and Arsenic-Containing Nucleophiles," Mendeleev Communications 1(4):128-129, 1991.

Kondo, S., et al., "Synthesis of Polymer-Supported Tetraphenylphosphonium Bromides as Effective Phase-Transfer Catalysts at Alkaline Conditions," Die Makromolekulare Chemie, Rapid Communications 11(7):309-313, Jul. 1990.

Lambert, C., et al., "Cationic π-Electron Systems With High Quadratic Hyperpolarisability," Journal of the Chemical Society, Perkin Transactions 2, 6:964-974, Jun. 2001.

Li, W., et al., "Synthesis of 3-Pyridylboronic Acid and Its Pinacol Ester. Application of 3-Pyridylboronic Acid in Suzuki Coupling to Prepare 3-Pyridin-3-ylquinoline," Organic Syntheses 81:89-93, 2005.

Lu, S.-M., and H. Alper, "Hydroformylation Reactions With Recyclable Rhodium-Complexed Dendrimers on a Resin," Journal of the American Chemical Society 125(43):13126-13131, Oct. 2003.

Maercker, A., "The Wittig Reaction," vol. 14, Chap. 3, "Organic Reactions," John Wiley and Sons, Hoboken, N.J., 1965, pp. 270-271, 402-413.

Manabe, K., "Asymmetric Phase-Transfer Alkylation Catalyzed by a Chiral Quaternary Phosphonium Salt With a Multiple Hydrogen-Bonding Site," Tetrahedron Letters 39(32):5807-5810, Jun. 1998.

Manabe, K., "Synthesis of Novel Chiral Quaternary Phosphonium Salts With a Multiple Hydrogen-Bonding Site, and Their Application to Asymmetric Phase-Transfer Alkylation," Tetrahedron 54(48):14465-14476, Sep. 1998.

Merrifield, R.B., “Solid Phase Peptide Synthesis. I. The Synthesis of a Tetrapeptide,” Journal of the American Chemical Society 85(14):2149-2154, Jul. 1963.
Molteni, V., et al., “Identification of a Small-Molecule Binding Site at the Dimer Interface of the HIV Integrase Catalytic Domain,” Acta Crystallographica, Section D: Biological Crystallography D57(Pt. 4):536-544, Apr. 2001.
Poupon, J.-C., et al., “New Supported Reagents: Solubility Controlling Group® Based on a Phosphonium Salt,” 4e Symposium International de Synthèse Organique de l’Université de Montréal (SISOUM), Apr. 29, 2005,15 pages.
Poupon, J.-C., et al., “Solubility Control Group (SCG), Application 1: SCG-Supported Organic Substrates,” poster, Informex, Las Vegas, Nevada, Jan. 17-20, 2005, 1 page.
Prodanchuk, N.G., et al., “Biological Activity of Phosphonium Hydrasones,” Fiziologicheski Aktivnye Veshchestva 19:60-67, 1987.
Quarrell, R., et al., “Structure and Properties of TentaGel Resin Beads: Implications for Combinatorial Library Chemistry,” Molecular Diversity 1(4):223-232, Aug. 1996.
Shuttleworth, S.J., et al., “Functionalised Polymers: Recent Developments and New Applications in Synthetic Organic Chemistry,” Synthesis 11(1997):1217-1239, Nov. 1997.
Su, Y.Z., et al., “Amorphous 2,3-Substituted Thiophenes: Potential Electroluminescent Materials,” Chemical Materials 14(4):1884-1890, Apr. 2002.
Tzschucke, C.C., et al., “Modern Separation Techniques for the Efficient Workup in Organic Synthesis,” Angewandte Chemie International Edition 41(4):3964-4000, Nov. 2002.
Yao, Q., “A Soluble Polymer-Bound Ruthenium Carbene Complex: A Robust and Reusable Catalyst for Ring-Closing Olefin Metathesis,” Angewandte Chemie International Edition 39(21):3896-3898, Nov. 2000.

PHOSPHONIUM SALTS DERIVATIVES AND USES THEREOF

CROSS-REFERENCE TO RELATED APPLICATIONS

The present application is a divisional application of U.S. application Ser. No. 11/539,075, filed Oct. 5, 2006, which is continuation-in-part of International Patent Application No. PCT/CA2005/000523, filed Apr. 6, 2005, which claims the benefit of U.S. Provisional Application No. 60/560,592, filed Apr. 9, 2004. The above-mentioned applications are incorporated herein by reference in their entirety.

TECHNICAL FIELD

The present invention relates to improvements in the field organic chemistry. In particular, this invention relates to novel chemicals and more particularly to novel supports, solubility controlling auxiliaries and reagents.

BACKGROUND OF THE INVENTION

Tremendous effort has been made during the last decades to develop novel supports to facilitate organic synthesis. These supports have been used not only to carry out multi-step organic synthesis of organic molecules (Horton, D. A.; Bourne, G. T.; Smythe, M. L., *Chem. Rev.* 2003, 103, 893-930; and Benaglia, M.; Puglisi, A.; Cozzi, F., *Chem. Rev.* 2003, 3401-3429) but also to bind catalysts, reagents and scavengers to facilitate the purification process of a product or to facilitate the recovery of a potentially expensive catalyst or reagent (Kirschning, A.; Monenschein, H.; Wittenberg, R., *Angew. Chem. Int. Ed.* 2001, 40, 650-679). Various strategies that have been used are detailed within the next paragraphs.

A first approach initiated by Merrifield (Merrifield, R. B., *J. Am. Chem. Soc.* 1963, 85, 2149) was to use functionalized cross-linked, insoluble polymers. This solid-phase technology revolutionized the polypeptide and polynucleotide synthesis and was soon employed to develop solid-supported reagents and catalysts (Shuttleworth, S. J.; Allin, S. M.; Sharma, P. K., *Synthesis* 1997, 1217-1239; Bhalay, G.; Dunstan, A.; Glen, A., *Synthesis* 2000, 1846-1859). The main advantages of this solid-phase methodology are the ease of separation of the supported species from the reaction mixture and the high loadings allowed in the preparation of the functionalized polymer. However, the major drawback is the lower reactivity of the solid-supported reagent compared to that observed for the corresponding homogeneous reaction because of limited diffusion of the substrate into the polymer backbone. Therefore, an excess of reagent or scavenger must usually be used to force the reaction to completion. Furthermore, the synthesis of the functionalized polymer may be sometimes troublesome since reactive functionality has to be introduced on the polymer backbone.

Silica bound scavengers or reagents have been developed (Heckel, A.; Seebach, D., *Angew. Chem. Int. Ed.* 2000, 39, 163-165). The silica rigid and non-swelling backbone eliminates solvent compatibility and kinetic issues. Nevertheless these reagents are more difficult to produce due to loading control issue and the difficulty in characterizing the silica gel once prepared.

As an attempt to restore the classical homogeneous organic chemistry conditions, the replacement of insoluble resins by a soluble polymer support became a popular modification (Dickerson, T. J.; Reed, N. N.; Janda, K. D., *Chem. Rev.* 2002, 102, 3325-3344; and Bergbreiter, D. E., *Chem. Rev.* 2002, 102, 3345-3384). The non-cross linked support is typically soluble is some solvents and insoluble in others. However, the difficulties associated with this solution-phase technique were to obtain a reasonable loading capacity of the reagent since higher loadings usually led to unpredictable solubility properties. The ability to isolate the polymer cleanly from all the other components at the end of a reaction can also be a problem.

Among the soluble polymers: polyethylene polyethylene glycols (PEGs) (Han, H.; Janda, K. D., *J. Am. Chem. Soc.* 1996, 118, 7632-7633; and Yao, Q., *Angew. Chem. Int. Ed.* 2000, 39, 3896-3898) and non cross-linked polystyrene (NCLP) (Enholm, E. J.; Gallagher, M. E.; Moran, K. M.; Lombardi, J. S.; Schulte II, J. P., *Org. Lett.* 1999, 1, 689-691; and Charette, A. B.; Boezio, A. A.; Janes, M. K., *Org. Lett.* 2000, 2, 3777-3779) have been by far the most widely used for the recovery and the recycling of reagent or catalyst.

A recent approach used solid-support derived from ring-opening metathesis polymerisation (ROMP) (Barrett, A. G. M.; Hopkins, B. T.; Köbberling, *J. Chem. Rev.* 2002, 102, 3301-3324). Typically, the key transformations are conducted in solution to afford the monomer. A subsequent ring-opening metathesis polymerization using expensive ruthenium catalysts gives a polymer witch can be easily modified and optimized. Thus, the polymer could be prepared as either soluble or insoluble species. Nevertheless the functional groups compatible with the metathesis are limited and the need to precipitate selectively the polymer remains a major issues that requires extensive optimization.

A complementary approach involves linking of a catalyst or reagent on a dendrimeric structure (Ji, B. M.; Yuan, Y.; Ding, K. L.; Meng, A. B., *Chem.-Eur. J.* 2003, 9, 5989-5996; Lu, S. M.; Alper, H., *J. Am. Chem. Soc.* 2003, 125, 13126-13131; and Garber, S. B.; Kingsbury, J. S.; Gray, B. L.; Hoveyda, A. H., *J. Am. Chem. Soc.* 2000, 122, 8168-8179). One advantage is that the catalyst can be easily recovered and potentially reused, however, the synthetic sequence to build the dendrimeric structure is most of the times quite tedious since lengthy organic reaction sequences are usually required to build up the optimal system.

Another area is the ionic liquid chemistry (Tzschucke, C. C.; Markert, C.; Bannwarth, W.; Roller, S.; Hebel, A.; Haag, R., *Angew. Chem. Int. Ed.* 2002, 41, 3964-4000). These liquids are prepared by alkylation of the corresponding pyridine, imidazole, amine or phosphine with an alkyl halide to form the pyridinium, imidazolium, ammonium or the phosphonium salt. Then, the desired anion is installed by ion exchange with the alkali salt or by using an ion-exchange resin. This modification allows modulation of the solubility properties and melting point of the ionic liquid. The most popular ionic liquid is the $[BMIM]^+[X]^-$ (BMIM=1-n-butyl-3-methylimidazolium, X=OTf, $BF_4$, $PF_6$, $SbF_6$). As ionic liquids are highly polar and non-coordinating solvent, they dissolve easily transition-metal complexes mainly without changing their properties. Thus, the principal ionic liquids application is the domain of the recoverable catalyst. The ionic liquid phase can be reused and ligands bearing an ionic group can easily be designed. However most of reactant species must be solubilize in the ionic liquid by addition of a co-solvent or by heating. At the end of a reaction, product extraction could be difficult and the catalyst could leach out of the ionic liquid into the organic layer.

The fluorous phase is another useful alternative (Curran, D. P., *Angew. Chem. Int. Ed.* 1998, 37, 1174-1196). Reactants and catalysts can be labelled with a certain number of fluorine atoms to stay in the fluorous phase. Perfluoro protecting groups have been developed, allowing a substrate to be temporarily tagged for its purification on a fluorous reverse-phase column or to be soluble in the fluorous phase. Even if a co-solvent or a hybrid solvent (organic solvent bearing few fluorine atoms) are added to adjust the solubility, this methodology remain somewhat specific since the molecules must bear a number of fluorine atoms.

Reagents bearing basic or acidic moieties have also been developed. The major drawback from this system comes from the presence of a relatively reactive group (acid or basic) within the reagent and they have not been used that much in synthesis.

SUMMARY OF THE INVENTION

It is therefore an object of the present invention to provide a support which would overcome the drawbacks of the prior art.

According to one aspect of the invention, there is provided the use of a compound of formula (I):

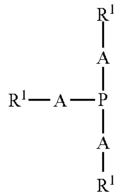

(I)

wherein

A is selected from the group consisting of furyl, phenyl, pyridyl, naphthyl, and thiophenyl; and $R^1$ is selected from the group consisting of a hydrogen atom, a halogen atom, —OH, —OMe, —SMe, —SPh, —SH, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl and $C_1$-$C_6$ hydroxyalkyl;

as a solubility controlling auxiliary.

According to another aspect of the invention, there is provided the use of a compound of formula (II):

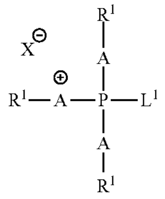

(II)

wherein

A is selected from the group consisting of furyl, phenyl, pyridyl, naphthyl, and thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

$L^1$ is a linker; and $X^-$ is selected from the group consisting of $F^-$, $Cl^-$, $Br^-$, $I^-$, $ClO^-$, $PF_6^-$, $N_3^-$, $BF_4^-$, $SbF_6^-$, $BH_4^-$, $RuO_4^-$, $N(SO_2CF_3)_2^-$, $CF_3SO_3^-$ (or triflate or TfO—), a conjugate base of an organic acid, an acetate and, an amino acid carboxylate, as a solubility controlling auxiliary.

According to still another aspect of the invention, there is provided the use of a compound of formula (I), as previously defined, for controlling solubility of a molecule. The molecule is attached to the phosphorus atom of the compound of formula (I) or to a linker attached to the phosphorus atom.

According to yet another aspect of the invention, there is provided the use of a compound of formula (I), as previously defined, as a solubility controlling fragment of a molecule. The compound of formula (I) being attached to the rest of the molecule by the phosphorus atom.

According to yet another aspect of the invention, there is provided the use of a compound of formula (II), as previously defined, as a solubility controlling fragment of a molecule. The compound of formula (II) being attached to the rest of the molecule by means of the linker $L^1$.

Applicants have found that by using a compound of formula (I) or (II), it is possible to provide an efficient and simple support which has a good loading capacity. Such a support is also particularly interesting since it has a substantially low molecular weight and it can be used in various reaction media. Applicants have also found that compounds of formula (I) and (II) can be used as efficient solubility controlling auxiliaries which are covalently bonded to a substrate or molecule. These solubility controlling auxiliaries which can act as soluble supports thus offer an efficient alternative in organic synthesis. In fact, they permit to overcome the major drawbacks of the soluble supports of the prior art.

According to a further aspect of the invention, there is provided a method for controlling the solubility of a molecule, comprising the step of attaching the molecule to a compound of formula (I), as previously defined. The molecule is attached to the phosphorus atom of the compound of formula (I).

According to still a further aspect of the invention, there is provided a method for controlling the solubility of a molecule, comprising the step of attaching the molecule to a compound of formula (II), as previously defined. The molecule is attached to the linker $L^1$.

According to another aspect of the invention, there is provided a method for using a compound of formula (I), as previously defined, the method comprises the step of attaching a molecule to the phosphorus atom of the compound of formula (I) so as to control the solubility of the molecule.

According to another aspect of the invention, there is provided a method for using a compound of formula (II), as previously defined, the method comprises the step of attaching a molecule to the linker of the compound of formula (I) so as to control the solubility of the molecule.

Applicants have found that by using any one of the above methods, it is possible to control the solubility of a molecule or a substrate by using a compound of formula (I) or (II). Such methods are efficient since using a simple auxiliary which can be used in various reaction mediums.

According to another aspect of the invention, there is provided a method for carrying out a chemical reaction comprising the step of using a compound of formula (I), as previously defined, as a solubility controlling auxiliary.

According to another aspect of the invention, there is provided a method for carrying out a chemical reaction comprising the steps of:

a) attaching a substrate on a solubility controlling auxiliary of formula (I), as previously defined, the substrate being attached to the phosphorus atom of the compound of formula (I) or to a linker attached to the phosphorus atom;

b) chemically modifying the substrate so as to obtain a chemically modified substrate attached to the solubility controlling auxiliary; and c) cleaving the chemically modified substrate from the solubility controlling auxiliary.

According to another aspect of the invention, there is provided a method for carrying out a chemical reaction comprising the steps of:

a) providing a compound of formula (I), as previously defined, the compound of formula (I) having a substrate attached to the phosphorus atom;

b) solubilizing the compound of formula (I) having the substrate attached thereto, in a first solvent so as to obtain a solution;

c) chemically modifying the substrate;

d) adding a second solvent to the solution so as to cause the compound of formula (I) having the chemically modified substrate attached thereto to precipitate; and e) separating the precipitate from the solution, thereby isolating the compound of formula (I) having the chemically modified substrate attached thereto.

Step (e) is preferably carried out by filtering the precipitate from the solution. The method can further comprises the step of cleaving the chemically modified substrate from the compound of formula (I) and recovering the chemically modified substrate and the compound of formula (I). The chemically modified substrate and the compound of formula (I) can be separately isolated and/or purified.

According to another aspect of the invention, there is provided a method for carrying out a chemical reaction comprising the steps of:

a) providing a compound of formula (IIIB);

(IIIB)

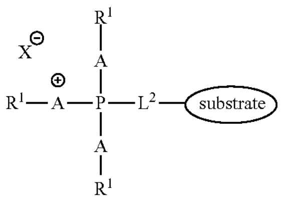

wherein

A is selected from the group consisting of furyl, phenyl, pyridyl, naphthyl, and thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl and $C_1$-$C_{12}$ heteroaryl, $C_1$-$C_{12}$ heterocyclyl, and $C_1$-$C_6$ hydroxyalkyl;

$L^2$ is a linker or a chemical bond;

$X^-$ is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate;

the substrate being a chemical substrate to be modified;

b) solubilizing the compound of formula (IIIB) in a first solvent so as to obtain a solution;

c) chemically modifying the substrate so as to obtain a compound of formula (IV):

(IV)

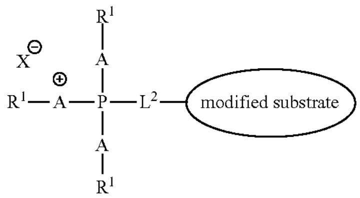

d) adding a second solvent to the solution so as to cause the compound of formula (IV) to precipitate;

e) separating the precipitate from the solution, thereby isolating the compound of formula (IV).

Step (e) is preferably carried out by filtering the precipitate from the solution. The method can further comprises the step of cleaving the modified substrate from the phosphorus atom or from the linker and recovering the modified substrate. The modified substrate is preferably isolated and/or purified. The method can further comprises the step of recovering a compound of formula (II):

(II)

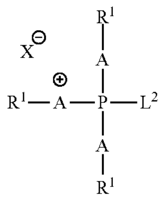

wherein $R^1$, A, $X^-$ and $L^2$ are as previously defined, or another salt thereof.

Applicants have found that by using the above mentioned methods for carrying out a chemical reaction, it is possible to use a compound of formula (I) or a derivative thereof as a support. By attaching a substrate on the phosphorus atom or to a linker attached to the phosphorus atom of a compound of formula (I) or a derivative thereof, it is possible to carry out various chemical reactions by avoiding tedious tasks usually necessary in organic chemistry. In fact, by doing so, chemical reactions can be done similarly then when performing a reaction on a solid support such as a resin. However, in the above mentioned methods, the support is a solubility controlling auxiliary which is simple and which has a substantially low molecular weight and a good loading capacity. Moreover, the solubility controlling auxiliary can be recycled.

According to another aspect of the invention, there is provided a compound of formula (V) (VI) or (VII):

(V)

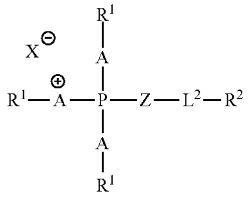

-continued (VI)

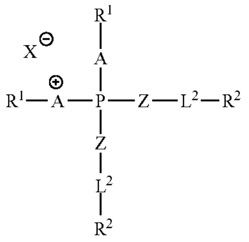

(VII)

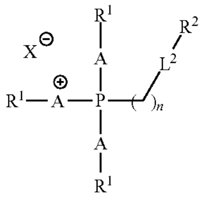

wherein

A and Z are the same or different, each represents a furyl, phenyl, pyridyl, naphthyl, or a thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

$R^2$ is Br, $N_3$, OH, $CH_2OH$, COOH, CHO, $CH{=}CH_2$, a linking moiety or a chemical reagent;

$X^-$ is selected from the group consisting of $F^-$, $Cl^-$, $Br^-$, $I^-$, $ClO_4$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate;

$L^2$ is a linker or a chemical bond; and n is an integer having a value of 0 to 6.

According to another aspect of the invention, there is provided a compound of formula (IX) or (X):

(IX)

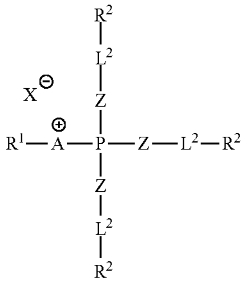

(X)

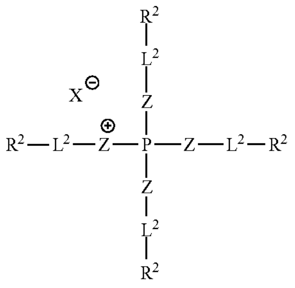

wherein

A and Z are the same or different, each represents a furyl, phenyl, pyridyl, naphthyl, or a thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

$R^2$ is Br, $N_3$, OH, $CH_2OH$, COOH, CHO, $CH{=}CH_2$, a linking moiety or a chemical reagent;

$X^-$ is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate; and $L^2$ is a linker or a chemical bond.

According to another aspect there is provided a compound of formula (XI) (XII) or (XIII):

(XI)

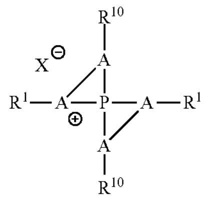

(XII)

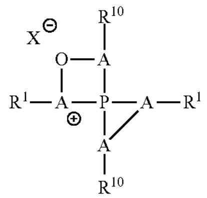

(XIII)

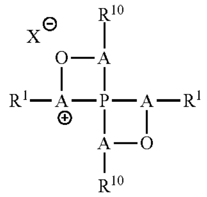

wherein

A represents a furyl, phenyl, pyridyl, naphthyl, or a thiophenyl;

$R^1$ and $R^{10}$ are same or different and selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_g$ cycloalkyl, $C_1$-$C_{12}$ heteroaryl, $C_1$-$C_{12}$ heterocyclyl, and $C_1$-$C_6$ hydroxyalkyl; and $X^-$ is selected from the group consisting of $F^-$, $Cl^-$, $Br^-$, $F^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate, an optically active isomer thereof, or a racemic mixture thereof.

It was found that the compounds of formulas (V) to (XIII) are very useful in organic synthesis and they permits to carry out chemical reactions in a simplified manner. In fact, these phosphonium supported reagents offer an alternative manner to carry out traditional reactions by avoiding several tedious tasks of organic synthesis. In particular, purification steps and steps related to elimination of by-products can be considerably simplified by using such compounds. Moreover, these compounds have an efficient loading capacity and can be easily prepared.

The expression "solubility controlling auxiliary" as used herein refers to an auxiliary or a molecule which can be covalently bonded to at least one other molecule in order to control the solubility of the other molecule. Preferably, the solubility controlling auxiliaries of the present invention are soluble supports. In certain conditions, the auxiliary and the other molecule attached thereto are soluble in a solvent and in other conditions, the auxiliary and the other molecule attached thereto precipitate in the solvent.

The term "alkyl" as used herein refers to a straight or branched alkyl. The alkyl can be unsubstituted or substituted with a substituent selected from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "aryl" has used herein refers to a cyclic or polycyclic aromatic ring. The aryl can be, for example, unsubstituted or substituted with 1 to 3 substituents selected from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "heteroaryl" has used herein refers to an aromatic cyclic or fused polycyclic ring system having at least one heteroatom selected from the group consisting of N, O, and S. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on. These heteroaryl groups can be unsubstituted or substituted with 1 to 3 substituents selected from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "heterocyclyl" includes non-aromatic rings or ring systems that contain at least one ring having an at least one hetero atom (such as nitrogen, oxygen or sulfur). Preferably, this term includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl. The heterocyclyl can be, for example, unsubstituted or substituted with 1 to 3 substituents selected from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "cycloalkyl" has used herein refers to a hydrocarbon ring which may contain or not double bonds. The cycloalkyl ring may be unsubstituted or substituted by 1 to 3 substituents selected from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

In the present invention, compounds of formula (I) having a molecule attached thereto are preferably compounds of formula (IIIA):

(IIIA)

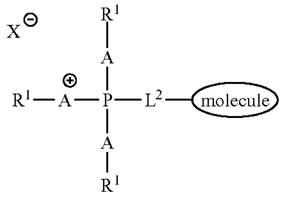

wherein $R^1$ and A are as previously defined;

$X^-$ is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate; and $L^2$ is a linker or a chemical bond.

In the present invention, compounds of formula (IA) and (IIA) can be used as an alternative to compounds of formula (I) and (II), respectively:

(IA)

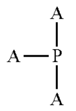

(IIA)

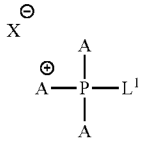

wherein

A is selected from the group consisting of furyl, phenyl, pyridyl, naphthyl, and thiophenyl, and is unsubstituted or substituted with 1 to 3 substituents, which are same or different, and selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl and $C_1$-$C_{12}$ heteroaryl, $C_1$-$C_{12}$ heterocyclyl, and $C_1$-$C_6$ hydroxyalkyl;

$X^-$ is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate;

$L^1$ is as previously defined.

Alternatively, each A can have two or three substituents.

In the present invention, the molecules or substrates to be attached to compounds of formulas (I) and (II), or attached to compounds of formulas (IIIA) and (IIIB), preferably have a molecular weight ranging from ranging from 40 to 1200 g/mol, more preferably from 50 to 1000 g/mol, and even more preferably from 60 to 700 g/mol. These molecules are advantageously organic reagents and they are preferably selected from the group consisting of an amine reagents, catalysts, ligands, chiral ligands linkers, coupling reagents, organic substrates, phosphine reagents, tin reagents, silicon reagents, and a scavengers.

In compounds of formula (II), the linker $L^1$ can be selected from the group consisting of:

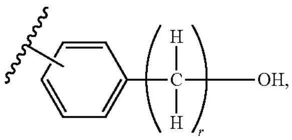

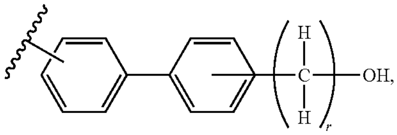

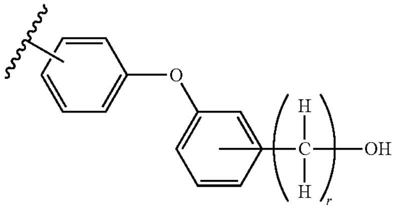

and

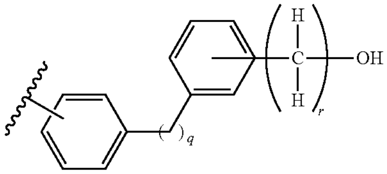

wherein r and q are integers having a value of 0 to 6.

The linker can also be an oxidized derivative of these compounds.

When compounds of formulas (I) or (II) are used as solubility controlling fragment of a molecule, the molecule advantageously have a molecular weight ranging from ranging from 40 to 3000 g/mol, preferably from 50 to 2000 g/mol, and more preferably from 60 to 1400 g/mol. Preferably, such a molecule is soluble in a first solvent selected from the group consisting of dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile and nitrobenzene. The molecule preferably precipitates in a mixture comprising the first solvent and a second solvent selected from the group consisting of diethylether ($Et_2O$), tetrahydrofuran (THF), hexanes, toluene, benzene, chlorobenzene, tetrachloromethane and t-butyl methyl ether. Advantageously, the molecule precipitates by adding the second solvent to a solution comprising the molecule substantially solubilized in the first solvent. The molecule can also be slightly soluble in a cosolvent selected from the group consisting of methanol, 2-propanol, acetone, and ethyl acetate. The molecule can thus be solubilized in a mixture comprising the first solvent and the cosolvent. Moreover, the molecule can precipitate by adding the second solvent to a solution comprising the molecule substantially solubilized in the mixture of the first solvent and the cosolvent. In particular ratios, the molecule can also be soluble in a mixture comprising the first solvent and the second solvent. In these compounds, A can have more than one $R^1$ substituent. As example A can have two or three $R^1$ substituents. In such a case, the $R^1$ substituents are the same or different.

Compounds of formulas (IIIA), (IIIB), (V), (VI), (VII), (VIII), (IX), (X), (XI), (XII), and (XIII) preferably have a molecular weight ranging from ranging from 40 to 3000 g/mol, preferably from 50 to 2000 g/mol, and more preferably from 60 to 1400 g/mol. These compounds can be so-called phosphonium supported reagents. These compounds are preferably soluble in a first solvent selected from the group consisting of dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile and nitrobenzene. They also preferably precipitate in a mixture comprising the first solvent and a second solvent selected from the group consisting of diethylether ($Et_2O$), tetrahydrofuran (THF), hexanes, toluene, benzene, chlorobenzene, tetrachloromethane and t-butyl methyl ether. Advantageously, they precipitate by adding the second solvent to a solution comprising the molecule substantially solubilized in the first solvent. These compounds can also be slightly soluble in a cosolvent selected from the group consisting of methanol, 2-propanol, acetone, and ethyl acetate. These compounds can thus be solubilized in a mixture comprising the first solvent and the cosolvent. Moreover, these compounds can precipitate by adding the second solvent to a solution comprising one of these compounds substantially solubilized in the mixture of the first solvent and the cosolvent. In particular ratios, these compounds can also be soluble in a mixture comprising the first solvent and the second solvent. In these compounds, A is preferably a phenyl, $R^1$ is preferably an hydrogen atom or a methyl and X is preferably $ClO_4$ or $PF_6$. More preferably, $R^1$ is an hydrogen atom. $R^2$ is preferably a chemical reagent selected from the group consisting of an amine reagent, a catalyst, a coupling reagent, a ligand, a chiral ligand, a phosphine reagent, a tin reagent, a silicon reagent, a boron reagent, and a scavenger. In these compounds, A can have more than one $R^1$ substituent. As example A can have two or three $R^1$ substituents. In such a case, the $R^1$ substituents are the same or different.

In the present invention compounds of formula (VA), (VIA), (VIIA) (IXA), (XIA), (XIIA), (XIIIA) and (XIVA) can be used as an alternative to compounds of formula (V), (VI), (VII), (IX), (XI), (XII), (XIII) and (X) respectively:

(VA)

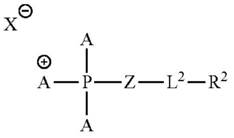

(VIA)

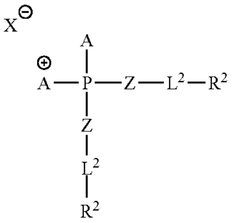

(VIIA)

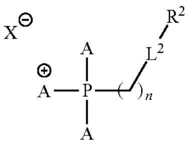

-continued (IXA)

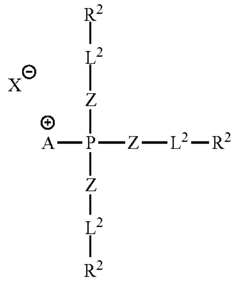

(XIVA)

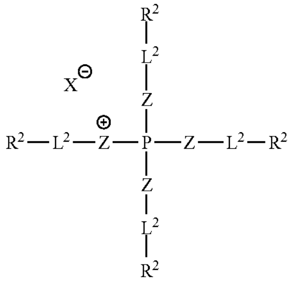

(XIA)

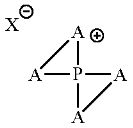

(XIIA)

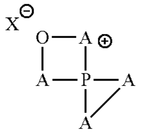

(XIIIA)

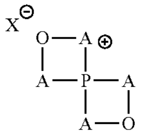

wherein each of said A independently represents a $C_6$-$C_{12}$ aryl (for example phenyl or naphthyl) or a $C_1$-$C_{12}$ heteroaryl (for example furyl, pyridyl, or thiophenyl);

each of said A is unsubstituted or substituted with 1 to 3 substituent(s) selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

each of said Z independently represents a $C_6$-$C_{12}$ aryl (for example phenyl or naphthyl) or a $C_1$-$C_{12}$ heteroaryl (for example furyl, pyridyl, or thiophenyl);

each of said Z is unsubstituted or substituted with 1 to 3 substituent(s) selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

$R^2$ is I, Cl, Br, $N_3$, OH, $CH_2OH$, COOH, CHO, N═C═O, CH═$CH_2$, a linking moiety or a chemical reagent;

$X^-$ is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $RuO_4^-$, $N(SO_2CF_3)_2^-$, $CF_3SO_3^-$, a conjugate base of an organic acid, an acetate and, an amino acid carboxylate, $L^2$ is a linker or a chemical bond; and n is an integer having a value of 0 to 12, preferably 0 to 6, an optically active isomer thereof, or a racemic mixture thereof.

The amine reagent can be one of a formula:

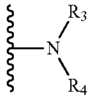

or

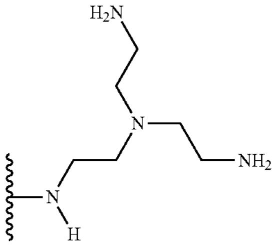

wherein $R^3$ and $R^4$ the are same or different and are selected from the group consisting of a hydrogen atom, $C_1$-$C_8$ alkyl, $C_2$-$C_8$ alkenyl, $C_2$-$C_8$ alkynyl, $C_6$-$C_{20}$ aralkyl, $C_6$-$C_{12}$ aryl, $C_3$-$C_8$ cycloalkyl, $C_1$-$C_{12}$ heterocyclyl, $C_1$-$C_6$ hydroxyalkyl and; or $R^3$ and $R^4$ are joined together to from a 5 or 6 membered heterocyclic ring;

the $C_1$-$C_{12}$ heterocyclyl being preferably selected from the group consisting of pyridine, piperidine, pyrrolidine, pyrrole, pyrimidine, cyclic guanidine, cyclic amidine, and oxazolidinone;

the 5 or 6 membered heterocyclic ring being preferably selected from the group consisting of pyridine, piperidine, pyrrolidine, pyrrole, pyrimidine, cyclic guanidine, cyclic amidine, and oxazolidinone.

The catalyst can be a ruthenium catalyst suitable for olefin metathesis reactions. The expression "ruthenium catalyst suitable for olefin metathesis reactions" has used herein refers to catalyst which can catalyze an olefin methathesis reaction. Such a catalyst is preferably a Grubbs-type catalyst. Preferably, the catalyst is selected from the group consisting of

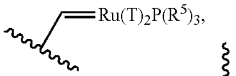

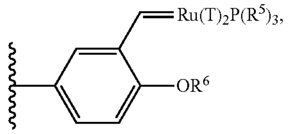

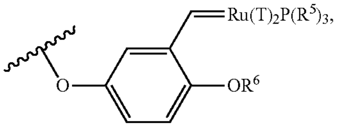

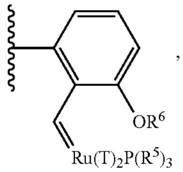

,

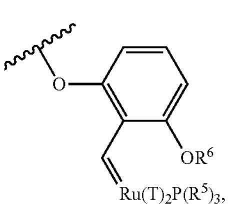

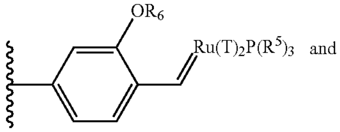

and

-continued

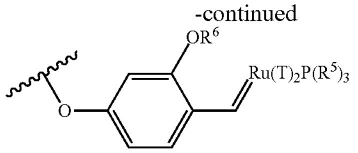

wherein $R_5$ is cylohexyl;

$R_6$ is selected from the group consisting of $C_1$-$C_6$ alkyl and $C_5$-$C_6$ cycloalkyl; and T is selected from the group consisting of Br, Cl, I, and OTf (triflate).

The phosphine reagent can be selected from the group consisting of

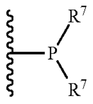

and

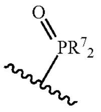

wherein $R^7$ is a $C_1$-$C_6$ alkyl, a $C_5$-$C_6$ cycloalkyl, or a phenyl group, or substituted phenyl, the phenyl being substituted by a hydrogen atom, halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, or $C_1$-$C_6$ hydroxyalkyl. Preferably, $R^7$ is a methyl group or a phenyl group.

The tin reagent can be selected from the group consisting of

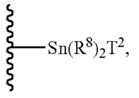

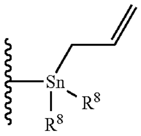

and

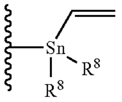

wherein $T^2$ is H, Br, Cl or OTf, and preferably Cl; and $R^8$ is a $C_1$-$C_6$ alkyl, preferably n-butyl.

The coupling reagent can be selected from the group consisting of

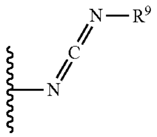

and

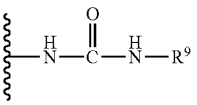

wherein $R^9$ is a $C_1$-$C_6$ alkyl or a $C_5$-$C_7$ cycloalkyl, and preferably a $C_6$ cycloalkyl.

The ligand can selected from the group consisting of bipyridines and bis(quinolines).

The chiral ligand can selected from the group consisting of oxazolines, bis(oxazolines), phosphines, N-heterocyclic carbenes, substituted binaphthols, 1,2-diols, 1,3-diols, 1,4-diols.

The scavenger can be selected from the group consisting of aldehydes, tertiary amines and sulfonic acid.

$R^2$ can be an amine or pyridine reagent of formula:

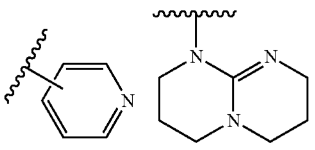

$R^2$ can also be an oxidizing reagent, which is preferably of formula:

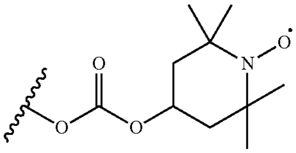

or

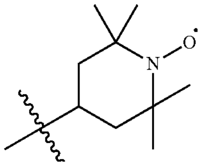

The silicon reagent can be of formula:

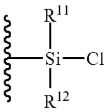

wherein $R^{11}$ and $R^{12}$ are same or different and selected from the group consisting of methyl, ethyl, isopropyl, tert-butyl and phenyl.

The linking moiety can be selected from the group consisting of

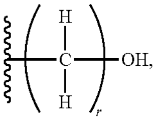

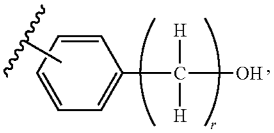

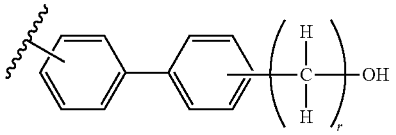

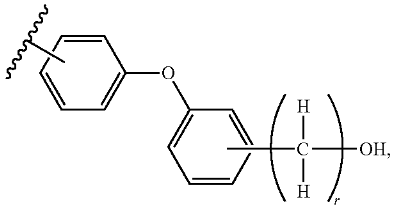

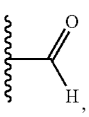

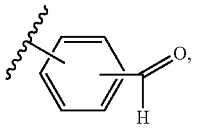

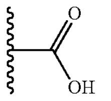

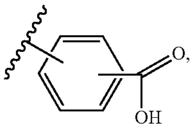

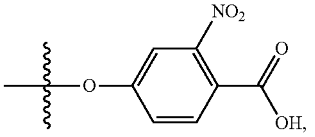

-continued

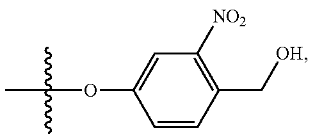

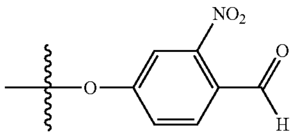

and

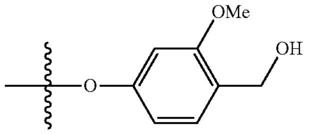

wherein r is an integer having a value of 0 to 6.

$L^2$ can be any suitable linker known to the person skilled in the art. In a non-limitative manner the linker can be selected from the group consisting of

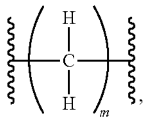

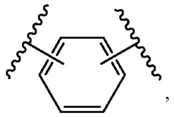

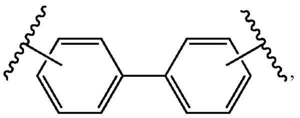

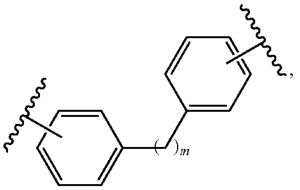

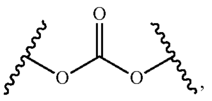

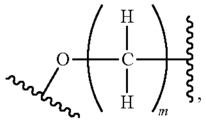

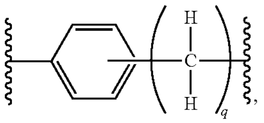

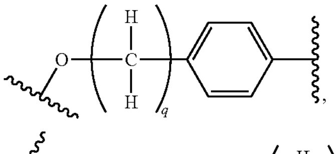

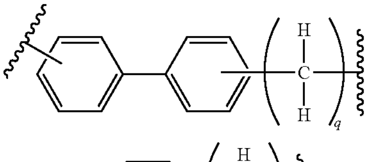

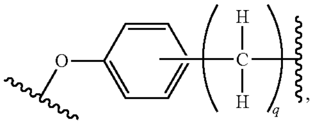

-continued

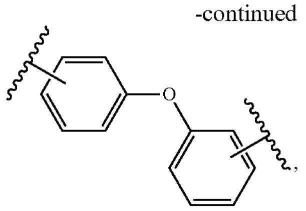

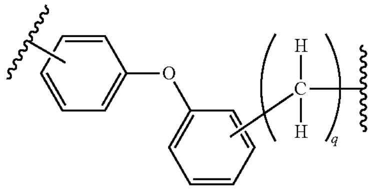

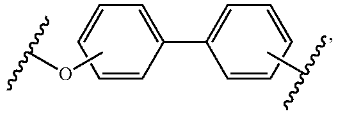

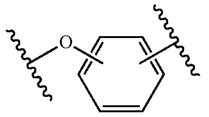

and

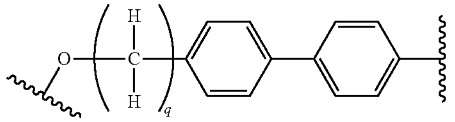

wherein m is an integer having a value of 1 to 8 and q is an integer having a value of 0 to 6. In these linkers, the O atoms could also be replaced with S atoms. In fact, the corresponding thioethers could also be used as linkers. In certain molecules, $L^2$ could be simply an oxygen atom or a sulphur atom, a $C_1$-$C_6$ alkyl, $C_1$-$C_6$ akenyl or $C_1$-$C_6$ alkynyl.

The compounds of the present invention can thus efficiently be used as phosphonium supported reagents, solubility controlling fragments of molecules or substrates, solubility controlling auxiliaries, supports or soluble supports.

In the methods of the present invention, when two solvents are used, the first solvent is preferably selected from the group consisting of dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile and nitrobenzene. The second solvent is preferably selected from the group consisting of diethylether ($Et_2O$), tetrahydrofuran (THF), hexanes, toluene, benzene, chlorobenzene, tetrachloromethane and t-butyl methyl ether. These compounds can also be slightly soluble in a cosolvent selected from the group consisting of methanol, 2-propanol, acetone, and ethyl acetate. These compounds can thus be solubilized in a mixture comprising the first solvent and the cosolvent. Moreover, these compounds can precipitate by adding the second solvent to a solution comprising one of these compounds substantially solubilized in the mixture of the first solvent and the cosolvent. In particular ratios, these compounds can also be soluble in a mixture comprising the first solvent and the second solvent.

According to another aspect of the invention there is provided a method for separating two different compounds from one another, each compound being a compound according to the present invention or a derivative thereof, the method comprising:

a) selecting a solvent or a mixture of solvents adapted to selectively precipitate one of the compounds with respect to the other; and b) mixing the compounds or derivative thereof with the solvent or mixture of solvents so as to selectively precipitate one of the compound.

The expression "derivative thereof" as used herein refers to a derivative which substantially has the same backbone than the compound. Such a derivative can be considered by the person skilled in the art as a close intermediate of the compound. The derivative differs only from the compound by way of a reaction (such an oxidation or a reduction) which is carried out in a single step. Non-limitative examples of a compound and a derivative thereof can be the following couples: compounds (8) and (4), compounds (40) and (41); and compounds (3) and (3'), which are all described subsequently.

Suitable solvent conditions for selectively precipitating one of the compounds can be provided by using the previously mentioned first solvent and/or second solvents systems. Alternatively, use of the cosolvent can also be made.

Preferably precipitation conditions for one of the compounds (taken alone) are first determined. If these conditions permits to precipitate the first compound tested and then subsequently if they permit to prevent the second compound (taken alone) from precipitating, these conditions (choice of solvents) can thus permit to selectively precipitate the first compound with respect to the second compound when the two are mixed together.

DESCRIPTION OF PREFERRED EMBODIMENTS

The following non-limiting examples further illustrate the invention.

Various examples of phosphonium salts derivatives have been prepared. Moreover, these compounds have been used in a plurality of different reactions.

EXAMPLE 1

Phosphonium Supported Triphenylphosphine (1)

1

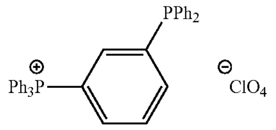

Preparation of the supported triphenylphosphine of formula (1) was carried out through synthesis of intermediates compounds (2) and (3).

2

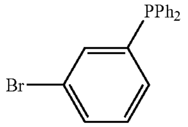

To a solution of 1,3-dibromobenzene (7.4 mL, 61 mmol, 1.05 equiv) in THF (70 mL, 0.9 M) at −90° C. was added n-BuLi (2.5 M) (25.5 mL, 64 mmol, 1.10 equiv) dropwise. The reaction mixture was stirred 45 min then diphenylchlorophosphine (10.7 mL, 58 mmol, 1.0 equiv) was added dropwise and the resulting dark brown solution was warmed to room temperature for 15 min and filtered through a small pad of Celite. The mixture was concentrated under reduced pressure and the residue was purified by flash chromatography ($Et_2O$/hexane, 0:100-5:95) to afford (3-bromophenyl)diphenylphosphine (2) (18.1 g, 91%) as a viscous colorless oil, which was characterized as follows:

$^1$H NMR (400 MHz, $CDCl_3$) δ 7.50-7.20 (m, 14H)

$^{13}$C NMR (100 MHz, $CDCl_3$) δ 140.7 (d, J=15.6 Hz), 136.4 (d, J=11.0 Hz), 136.1 (d, J=20.1 Hz), 133.9 (d, J=19.7 Hz), 132.2 (d, J=19.3 Hz), 131.8 (s), 130.2 (d, J=6.6 Hz), 129.2 (s), 128.8 (d, J=7.0 Hz), 123.3 (d, J=6.8 Hz).

IR (film) 1954 (C=C), 1882 (C=C), 1813 (C=C), 1574, 1556, 1460, 1433, 1391, 1090, 1066 $cm^{-1}$.

LRMS (APCI, Pos) calcd for $C_{18}H_{15}P^{79}Br$ $[M+H]^+$: 341.0 m/z, observed 341.0, calcd for $C_{18}H_{15}P^{81}Br$ $[M+H]^+$: 343.0 m/z, observed 343.0.

3

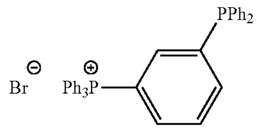

To a solution of nickel (II) bromide (dry under vacuum for 2 h at 140° C.) (3.6 g, 16 mmol, 0.5 equiv) in benzonitrile (dry overnight on activated 4 A molecular sieves) (250 mL) was added triphenylphosphine (26.0 g, 49 mmol, 3 equiv). The solution was heated under reflux for 15 min and then cooled to room temperature. (3-bromophenyl)diphenylphosphine (2) (11.1 g, 32.5 mmol, 1.0 equiv) in benzonitrile (20 mL plus rinse 5 mL) was added to the solution. The resulting solution was heated under reflux for 4 h then cooled to room temperature. A 10% (w/w) aqueous solution of potassium bromide (250 mL) was added. The layers were separated, and the aqueous layer was washed two times with $CH_2Cl_2$ (250 mL). The organic layer was washed three times with water (100 mL) and dried over anhydrous $MgSO_4$, filtered, and concentrated under reduced pressure. To the resulting solution was added hexane (750 mL) to precipitate the crude product. The precipitate was filtered and washed with hexane and then dissolved in $CH_2Cl_2$ (20 mL). $Et_2O$ (150 mL) was then added and the mixture was filtered. The resulting solid was purified by flash chromatography ($MeOH/CH_2Cl_2$, 0:100-10:90) to afford (3-diphenylphosphinophenyl)triphenylphosphonium bromide (3) (>95% purity) as a white solid (15.3 g, 78%), which was characterized as follows:

mp 215-220° C.

$^1$H NMR (400 MHz, $CDCl_3$) δ 7.60-6.80 (m, 29H).

$^{13}$C NMR (100 MHz, $CDCl_3$) δ 141.3 (dd, J=18.8, 11.0 Hz), 138.6 (d, J=22.3 Hz), 136.3 (t, J=12.1 Hz), 134.7 (d, J=2.1 Hz), 133.5 (d, J=10.6 Hz), 133.2 (m), 133.0 (d, J=10.3 Hz), 132.5 (d, J=20.2 Hz), 129.8 (d, J=12.8 Hz), 129.7 (m), 128.7 (s), 127.9 (d, J=7.2 Hz), 117.1 (dd, J=86.9, 4.4 Hz), 115.8 (d, J=88.9 Hz). $^{31}$P (162 MHz, $CDCl_3$) δ 23.2, −4.5.

IR (film) 1974 (C=C), 1913 (C=C), 1827 (C=C), 1585, 1474, 1432, 1433, 1386, 1108 $cm^{-1}$.

LRMS (APCI, Pos) calcd for $C_{36}H_{29}P_2$ $[M]^+$: 523.2 m/z, observed 523.1.

1

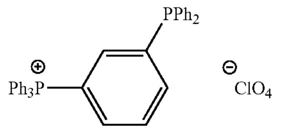

To (3-diphenylphosphinophenyl)triphenylphosphonium bromide (3) (15.0 g, 25 mmol, 1.0 equiv) in $CH_3CN$ (60 mL) was added $LiClO_4$ (2.9 g, 28 mmol, 1.1 equiv). After 2 h the mixture was concentrated under reduced pressure and diluted with $CH_2Cl_2$ (200 mL). The resulting mixture was washed with water (100 mL). The aqueous layer was washed with $CH_2Cl_2$ (100 mL). The organic solution was washed three times with water (50 mL), was dried over $MgSO_4$ and concentrated under reduced pressure. The crude product was diluted with $CH_2Cl_2$ (30 ml) and was precipitated by adding $Et_2O$ (150 mL) to afford (3-diphenylphosphinophenyl)triphenylphosphonium perchlorate (1) as a white solid. Two additional dissolution-precipitation sequence led to pure phosphonium perchlorate (14.7 g, 95%), which was characterized as follows:

$^1$H NMR (400 MHz, $CDCl_3$) δ 7.60-6.80 (m, 29H).

$^{13}$C NMR (100 MHz, $CDCl_3$) δ 141.3 (dd, J=18.4, 11.1 Hz), 138.7 (dd, J=22.1, 1.9 Hz), 136.5 (dd, J=14.2, 10.8 Hz), 134.6 (d, J=2.9 Hz), 133.6 (d, J=10.6 Hz), 133.2 (m), 133.1 (d, J=10.2 Hz), 132.6 (d, J=20.3 Hz), 129.6 (d, J=12.8 Hz), 129.5 (dd, J=17.2, 6.1 Hz), 128.7 (s), 127.9 (d, J=7.4 Hz), 117.1 (dd, J=87.3, 3.3 Hz), 115.8 (d, J=88.0 Hz).

$^{31}$P (162 MHz, $CDCl_3$) δ 23.2, −4.7.

IR (film) 1585, 1483, 1435, 1388, 1079 (Cl═O) $cm^{-1}$.

LRMS (APCI, Pos) calcd for $C_{36}H_{29}P_2$ $[M]^+$: 523.2 m/z, observed 523.1.

LRMS (APCI, Neg) calcd for $^{35}ClO_4$ $[M]^-$: 99.0 m/z, observed 99.0; $^{37}ClO_4$ $[M]^-$: 101.0 m/z, observed 101.1.

EXAMPLE 2

Use of Phosphonium Supported Triphenylphosphine (1) in a Mitsunobu Reaction

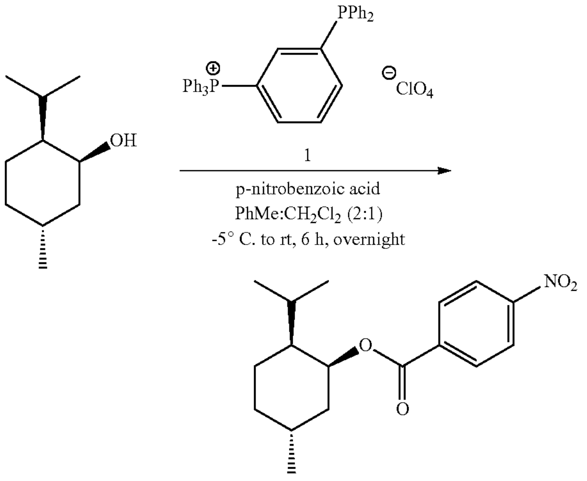

Menthol (156 mg, 1.0 mmol, 1 equiv) and (3-diphenylphosphinophenyl)triphenyl phosphonium perchlorate (1) (1.0 g, 1.6 mmol, 1.6 equiv) were dissolved in $CH_2Cl_2$ (5 mL). Toluene (10 mL) was then added and the solution was cooled to −5° C. Diethylazodicarboxylate (255 μl, 1.6 mmol, 1.6 equiv) was added dropwise over 5 min. Then 4-nitrobenzoïc acid (220 mg, 1.3 mmol, 1.3 equiv) was added and the solution was warmed slowly to room temperature over 3. After 9 h of stirring at room temperature, 25 mL of $Et_2O$ was added to the solution and the resulting mixture was filtered through cotton wool to recover the phosphine oxide (quant.) and the filtrate was concentrated under reduced pressure. The resulting crude product was dissolved in $CH_2Cl_2$ (1 mL) and hexane (9 mL) was added. The hydrazine and residual 4-nitrobenzoïc acid precipitated and the resulting mixture was filtered through cotton wool. The filtrate was concentrated under reduced pressure to afford pure ester (245 mg, 79%) that was identical in all respect to authentic material.

EXAMPLE 3

Phosphonium Supported Azodicarboxylate (Dead-Type) Reagent (4)

4

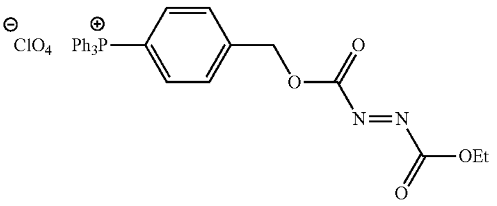

Preparation of the phosphonium supported azodicarboxylate (DEAD-type) reagent (4) was carried out through synthesis of intermediates compounds (5) to (8).

5

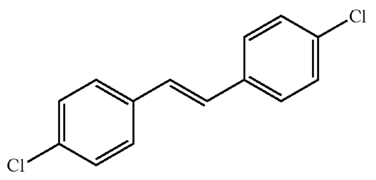

To zinc dust (flame dried under argon) (10.2 g, 156 mmol, 2.19 equiv) was added THF (215 mL) and the resulting mixture was cooled to −10° C. Titanium tetrachloride (8.3 mL, 76.0 mmol, 1.07 equiv) was carefully added to the solution. After 5 min 4-chlorobenzaldehyde (9.9 g, 70.0 mmol, 1.0 equiv) was added in one portion. The resulting mixture was heated under reflux for 20 h and then cooled to room temperature. A 10% (w/w) aqueous solution of potassium carbonate (150 mL) was added. The clear organic layer was collected and the aqueous layer was washed with $Et_2O$ (100 mL). The combined organic layers were concentrated under reduced pressure to afford a crude crystalline product washed with $Et_2O$ and dried under vacuum to afford E-4,4'-dichlorostyrene (5) as a pure white solid (7.9 g, 91%).

6

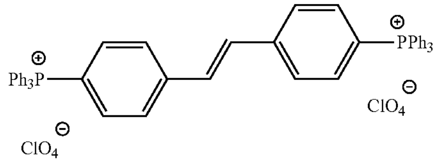

A solution of $NiBr_2$ (12.0 g, 54 mmol, 2 equiv), triphenylphosphine (28.0 g, 108 mmol, 4 equiv) and E-4,4'-dichlorostyrene (5) (6.8 g, 27 mmol, 1.0 equiv) in benzonitrile (250 mL, 0.1 M) was heated under reflux for 2 h. The solution was cooled to room temperature and $LiClO_4$ (23.0 g, 216 mmol, 8 equiv) was added in one portion. After 2 h of stirring, $CH_2Cl_2$ (500 mL) and $H_2O$ (400 mL) were added. The layers were separated, and the aqueous layer was washed twice with $CH_2Cl_2$ (250 mL). The organic solution was washed three times with water (200 mL), was dried over anhydrous $MgSO_4$, filtered and concentrated under reduced pressure. To the resulting mixture was added hexane (500 mL) to precipitate the crude product. The precipitate was washed with hexane (2×100 mL) followed by $Et_2O$ (2×100 mL) and it was dried under reduced pressure at 50° C. to afford a pure crystalline product of the bis(perchlorate) salt of bis(4,4'-triphenylphosphonium)styrene (6) as a white solid (20.7 g, 84%).

7

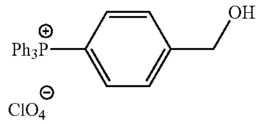

The bis(perchlorate) salt of bis(4,4'-triphenylphosphonium)styrene (6) (20.7 g, 23 mmol, 1.0 equiv) was diluted in $CH_2Cl_2$ (270 mL) and MeOH (70 mL). The resulting milky mixture was cooled to −78° C. and ozone was bubbled through the solution to saturate the solution (until appearance of the blue color). After stirring 45 min, $O_3$ was bubbled through the milky mixture to saturate the solution again. After 1 h of stirring, the solution became clear blue and it was purged with $O_2$ and argon. $NaBH_4$ (2.6 g, 69 mmol, 3.0 equiv) was then added to the solution. After 30 min of stirring, the solution was warmed to 0° C. for 1 h. A half saturated $NH_4Cl$ aqueous solution (100 mL) was carefully added. The layers were separated and the aqueous layer was washed twice with $CH_2Cl_2$ (50 mL). The organic solution was washed three times with water (50 mL) was dried over $MgSO_4$ and it was concentrated under reduced pressure. The crude product was diluted with $CH_2Cl_2$ (30 ml) and was precipitated with $Et_2O$ (150 mL). The crude precipitate was purified by flash chromatography ($MeOH/CH_2Cl_2$, 0:100-5:90) to afford pure (4-hydroxymethylphenyl)triphenylphosphonium perchlorate (7) as a white solid (16.9 g, 78%), which was characterized as follows:

mp 225-230° C.

$^{1}H$ NMR (400 MHz, $CD_2Cl_2$) δ 7.85-7.70 (m, 3H), 7.63-7.60 (m, 8H), 7.54-7.45 (m, 8H), 4.71 (s, 2H), 4.30 (bs, 1H). $^{13}C$ NMR (100 MHz, $CD_2Cl_2$) δ 150.8 (d, J=3.0 Hz), 135.4 (d, J=1.7 Hz), 134.4 (d, J=10.2 Hz), 134.3 (d, J=10.6 Hz), 130.3 (d, J=12.8 Hz), 128.1 (d, J=13.2 Hz), 117.7 (d, J=89.1 Hz), 115.0 (d, J=90.9 Hz), 63.4 (s). $^{31}P$ (162 MHz, $CD_2Cl_2$) δ 23.3. IR (film) 1777 (C═O), 1439, 1266, 1224, 1090 (Cl═O) $cm^{-1}$. LRMS (APCI, Pos) calcd for $C_{25}H_{22}O_1P_1$ $[M]^+$: 369.1 m/z, observed 369.1. LRMS (APCI, Neg) calcd for $^{35}ClO_4$ $[M]^-$: 99.0 m/z, observed 99.0; $^{37}ClO_4{}_{[M]}{}^-$: 101.0 m/z, observed 101.1. Elem. Anal. Calcd (%) for $C_{25}H_{22}ClO_5P$: C, 64.04; H, 4.73. found: C, 64.25; H, 4.92.

8

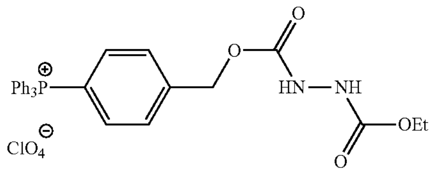

To a solution of triphosgene (1.3 g, 4.3 mmol, 0.43 equiv) in $CH_2Cl_2$ (100 mL) at −10° C. was added pyridine (2.1 mL, 26 mmol, 2.6 equiv) dropwise. The resulting mixture was warmed to room temperature for 10 min (became a clear limpid solution) then it was cooled to −78° C. (became a milky mixture). A solution of (4-hydroxymethylphenyl) triphenylphosphonium perchlorate (7) (4.7 g, 10 mmol, 1.0 equiv) in $CH_2Cl_2$ (50 mL, rinse with 10 mL) was added dropwise to the mixture which became a clear solution. After 10 min, ethyl carbazate (2.1 g, 20 mmol, 2.0 equiv) in $CH_2Cl_2$ (20 mL) was added dropwise to the solution. The solution became yellow and it was warmed slowly to 0° C. over 1.5 h. The resulting solution was washed with water (200 mL). The aqueous layer was washed twice with $CH_2Cl_2$ (100 mL). The organic solution was washed with water (100 mL), it was dried over $MgSO_4$ and concentrated under reduced pressure. The crude product was dissolved in $CH_2Cl_2$ (25 ml) and it was precipitated with $Et_2O$ (75 mL). This operation was repeated twice to afford the pure hydrazine (8) as a white solid foam (5.8 g, 97%), which has been characterized has follows:

$^{1}H$ NMR (400 MHz, $CDCl_3$) δ 8.00-7.85 (m, 3H), 7.85-7.70 (m, 8H), 7.70-7.65 (m, 8H), 7.31 (bs, 1H), 6.82 (bs, 1H), 5.26 (s, 2H), 4.12 (q, J=7.1 Hz, 2H), 1.20 (t, J=7.1 Hz, 3H).

$^{13}C$ NMR (100 MHz, $CDCl_3$) δ 156.7 (s), 156.3 (s), 144.8 (s), 135.7 (d, J=2.3 Hz), 134.5 (d, J=10.7 Hz), 134.3 (d, J=10.3 Hz), 130.7 (d, J=12.9 Hz), 129.0 (d, J=12.9 Hz), 117.5 (d, J=89.0 Hz), 116.5 (d, J=90.1 Hz), 65.6 (s), 61.9 (s), 14.4 (s).

$^{31}P$ (162 MHz, $CDCl_3$) δ 23.2.

4

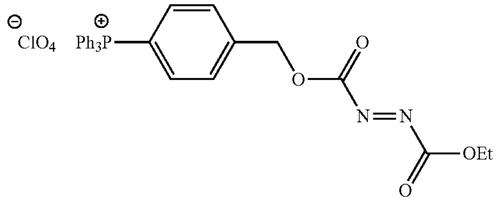

To a solution of the hydrazine (8) (3.0 g, 5.0 mmol, 1.0 equiv) in $CH_2Cl_2$ was added iodobenzene diacetate (2.4 g, 7.5 mmol, 1.5 equiv) in one portion. The solution was stirred 6 h then $Et_2O$ (200 mL) was added to precipitate the crude product. The crude product was diluted with $CH_2Cl_2$ (10 ml) and was precipitated with $Et_2O$ (100 mL). This operation was repeated four times to afford the DEAD equivalent (4) (>95% purity) as a yellow solid foam (2.5 g, 84%), which has been characterized as follows:

mp 85-80° C.

$^1$H NMR (400 MHz, $CDCl_3$) δ 7.95-7.65 (m, 19H), 5.59 (s, 2H), 4.49 (q, J=7.1 Hz), 1.41 (t, J=7.1 Hz). $^{13}$C NMR (100 MHz, $CDCl_3$) δ160.2 (s), 160.0 (s), 142.1 (d, J=2.9 Hz), 135.9 (d, J=2.6 Hz), 135.0 (d, J=10.6 Hz), 134.6 (d, J=10.3 Hz), 130.9 (d, J=12.9 Hz), 130.0 (d, J=13.1 Hz), 118.3 (d, J=89.5 Hz), 117.3 (d, J=89.1 Hz), 69.0 (s), 63.7 (s), 14.2 (s). $^{31}$P (162 MHz, $CDCl_3$) δ 23.2. IR (film) 1777 (C═O), 1439, 1266, 1224, 1090 (Cl═O) $cm^{-1}$. LRMS (APCI, Pos) calcd for $C_{36}H_{29}P_2$ $[M]^+$: 497.2 m/z, observed 497.1.

EXAMPLE 4

Use of Phosphonium Supported Dead Reagent (4) and of Phosphonium Supported Triphenylphosphine (1)

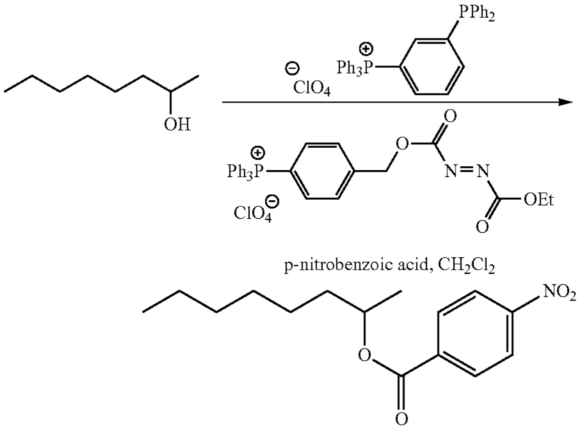

2-Octanol (26 mg, 0.2 mmol, 1.0 equiv), p-nitrobenzoic acid (40 mg, 1.2 mmol, 1.2 equiv) and (3-diphenylphosphinophenyl)triphenyl phosphonium perchlorate (1) (250 mg, 0.4 mmol, 2.0 equiv) were diluted in $CH_2Cl_2$ (1.5 mL). The solution was cooled to −5° C. and was added dropwise a solution of the phosphonium supported DEAD reagent (4) (240 mg, 0.4 mmol, 2.0 equiv) in $CH_2Cl_2$ (1 mL) over 5 min. The solution was warmed to room temperature overnight. The solution was added dropwise to a stirred solution of $Et_2O$ (15 mL). The resulting mixture was filtered through cotton wool and the filtrate was concentrated under reduced pressure. The resulting crude product was stirred with $CHCl_3$ (1 mL) to remove the insoluble residual p-pitrobenzoic acid and the resulting mixture was filtered through cotton wool. The filtrate was concentrated under reduced pressure to give the pure ester (86%). At the end of the reaction, the compound (3') was recovered:

3′

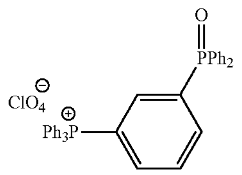

The compound (3') was characterized as follows:
white solid
M.p. 214-216° C.
$^1$H NMR (400 MHz, $CDCl_3$) 8.00-7.30 (m, 29H).

$^{13}$C NMR (100 MHz, $CDCl_3$) δ138.3 (dd, J=9.7, 2.9 Hz), 137.5 (dd, J=5.7, 3.2 Hz), 137.0 (t, J=11.0 Hz), 136.6 (dd, J=98.3, 11.2 Hz), 135.6 (d, J=2.7 Hz), 134.2 (d, J=10.3 Hz), 132.5 (d, J=2.5 Hz), 131.7 (d, J=10.0 Hz), 130.9 (t, J=11.5 Hz), 130.6 (d, J=10.6 Hz), 130.1 (d, J=105.2 Hz), 128.7 (d, J=12.8 Hz), 119.0 (dd, J=89.0, 11.6 Hz), 116.5 (d, J=89.0 Hz).

$^{31}$P (162 MHz, $CDCl_3$) 28.3, 23.3.

IR (film) 1585, 1483, 1435, 1388, 1079 (Cl═O) $cm^{-1}$.

LRMS (APCI, Pos) calcd for $C_{36}H_{29}P_2O$ $[M]^+$: 539.2 m/z, observed 539.1.

Recycling Compound (3') by Converting it into Compound (3)

To a 0° C. solution of Phosphine oxide (3') (200 mg, 0.30 mmol, 1.0 equiv) in Benzonitrile (3 mL, 0.1 M) was added N,N-Dimethylaniline (160 μL, 1,2 mmol, 4.0 equiv) and Trichlorosilane (63 μL, 0.62 mmol, 2.0 equiv). The solution was warmed to 170° C. over 2 h and became blue. The crude product was crunched with Hexane (20 mL). The crude product was diluted with $CH_2Cl_2$ (1 mL) and was crunched with $Et_2O$ (10 mL). This operation was repeated two times to afford a crude blue solid.

To the crude product (ca 0.30 mmol, 1.0 equiv) in $CH_3CN$ (1.5 mL) was added $LiClO_4$ (32 mg, 0.30 mmol, 1.0 equiv). After 2 h the mixture was concentrated under reduced pressure and diluted with $CH_2Cl_2$ (10 mL). The resulting mixture was washed with water (5 mL). The aqueous layer was washed with $CH_2Cl_2$ (2 mL). The organic solution was washed three times with water (2 mL), was dried over $MgSO_4$ and concentrated under reduced pressure. The crude product was diluted with $CH_2Cl_2$ (1 ml) and was crunched with $Et_2O$ (10 mL) to afford pure (3) as a white solid (173 mg, 93%).

Separation of the Triphenylphosphine Oxide (3') and Hydrazine (8) (Residues from the Mitsunobu Reaction) by Selective Precipitation:

To a solution of (3') (319 mg, 0.5 mmol, 1.0 equiv), (8) (300 mg, 0.5 mmol, 1.0 equiv) in $CH_2Cl_2$ (10 mL) at reflux was added $Et_2O$ (9 mL). Then was added under reflux dropwise $Et_2O$ (3 mL) during 15 min. The mixture was cooled to room temperature. The precipitate was recuperated (350 mg, (3'): (8)=3.8:1.0). This operation was repeated on the precipitate so as to afford pure (3') (227 mg, 71%).

EXAMPLE 5

Phosphonium Supported Ruthenium Catalyst (10)

10

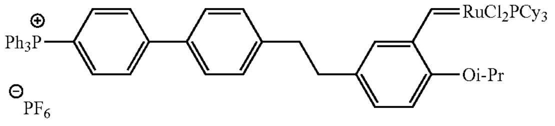

Preparation of the phosphonium supported ruthenium catalyst (10) was carried out through synthesis of intermediates compounds (11) to (14).

11

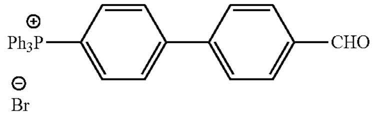

In an inert atmosphere of argon (with a high flow), 4-(4-bromophenyl)benzaldehyde (4 g, 15.33 mmol), $PPh_3$ (6.11 g, 22.99 mmol), and dry $NiBr_2$ (1.70 g, 7.66 mmol) were suspended in PhCN (160 ml). The resulting green reaction mixture was stirred at 200° C. for 4 h, and then cooled to r.t. The deep green reaction vessel was quenched with a 10% aq. soln. of KBr (200 ml), and extracted with $CH_2Cl_2$ (2×200 ml). The combined organic phases were washed with $H_2O$ (2×500 ml), brine (2×500 ml), dried ($Na_2SO_4$), and concentrated in vacuo to afford a brown oil. The resulting brown oil was taken up (in a flask) with hexane (500 ml), and the crude product glued on the faces of the flask as a thick oil. The hexane layer was separated, and this operation was carried out twice. The resulting thick oil was taken up with $CH_2Cl_2$ (small amount), and $Et_2O$ (200 ml) was added in order to precipitate the phosphonium salt. The flask was rotated vigorously, and the organic phase was decanted. This operation was done twice, affording the desired compound (11) as a yellow residue, which was pure enough to continue (4.4 g, 55%), has been characterized has follows:

$^1$H-NMR (400 MHz, $CDCl_3$): δ 10.02 (s, 1 H), 8.02 (d, J=6.72, 2 H), 7.94 (d, J=8.08, 2 H), 7.83 (m, 5 H), 7.72 (m, 8 H), 7.58 (m, 6 H). $^{13}$C-NMR (25 MHz, $CDCl_3$): δ 192.21, 147.00 (d, J=12.30), 144.17, 136.63, 136.24 (d, J=0.95), 135.48 (d, J=3.55), 134.71 (d, J=3.45), 131.26 (d, J=4.27), 130.87, 129.95 (d, J=4.40), 128.72, 118.21, 117.03. $^{31}$P (162 MHz, $CDCl_3$): δ 24.22 (s).

12

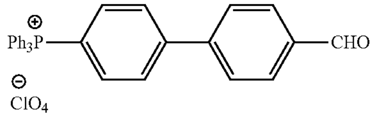

Compound (11) (3 g, 5.73 mmol) was dissolved in a solution of MeCN/$CH_2Cl_2$ (24 ml, 3:1), and $LiClO_4$ (1.22 g, 11.46 mmol) was added. The resulting reaction mixture was stirred at r.t. for 2 h, and then concentrated in vacuo to afford pale yellow residue. The residue was taken up with $CH_2Cl_2$ (50 ml), washed with $H_2O$ (2×50 ml), brine (2×50 ml), dried ($Na_2SO_4$), and concentrated in vacuo to afford a pale yellow residue. Treatment with $CH_2Cl_2$/$Et_2O$ led to the target compound (12), which was pure enough to continue (2.91 g, 94%), has been characterized has follows:

$^1$H-NMR (400 MHz, $CDCl_3$): δ10.03 (s, 1 H), 8.03-8.01 (dd, $J_1$=3.08, $J_2$=3.08, 2 H), 7.97 (d, J=8.36, 2 H), 7.90-7.84 (m, 5 H), 7.79-7.74 (m, 8 H), 7.69-7.63 (m, 6 H). $^{13}$C-NMR (25 MHz, $CDCl_3$): δ 192.34, 147.06, 144.47, 136.68, 136.19 (d, J=0.97), 135.56 (d, J=3.55), 134.83 (d, J=3.42), 131.21 (d, J=4.27), 130.91, 129.91 (d, J=4.35), 128.75, 118.41, 117.22. $^{31}$P-NMR (162 MHz, $CDCl_3$): δ 24.16 (s).

13

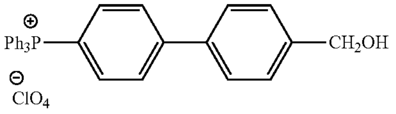

In an inert atmosphere of argon, compound (12) (707 mg, 1.30 mmol) was dissolved in $CH_2Cl_2$ (6.5 ml), and cooled to −78° C. $NaBH_4$ (54 mg, 1.43 mmol) in EtOH (1.5 ml) was added, and the reaction mixture stirred at −78° C. for 15 min, allowed to warm at r.t. over a period of 1.5 h, and finally quenched with a sat. aq. soln. of $NH_4Cl$ (10 ml). The aqueous phase was separated and extracted with $CH_2Cl_2$ (2×10 ml). The combined organic phases were washed with $H_2O$ (2×30 ml), brine (2×30 ml), dried ($Na_2SO_4$), and concentrated in vacuo to afford a yellow oil. Treatment with $CH_2Cl_2$/$Et_2O$ revealed compound (13) as a pale yellow foam which was pure enough to continue (600 mg, 84%), has been characterized has follows:

$^1$H-NMR (300 MHz, $CDCl_3$): δ 7.91-7.80 (m, 5 H), 7.72-7.68 (m, 6 H), 7.67-7.54 (m, 10 H), 7.34 (d, J=7.83, 2 H), 4.57 (s, 2 H), 3.39 (br. s., 1 H). $^{13}$C-NMR (25 MHz, $CDCl_3$): δ 148.44, 143.25, 137.26, 136.10 (d, J=1.00, CH-arom., 3 H), 135.34 (d, J=3.55, CH-arom., 2 H), 134.79 (d, J=3.42, CH-arom., 6 H), 131.15 (d, J=4.25, CH-arom., 6 H), 129.31 (d, J=4.40, CH-arom., 2 H), 128.09, 127.81. $^{31}$P (162 MHz, $CDCl_3$): δ 24.02 (s), −143.9 (sept, J=713 Hz).

14

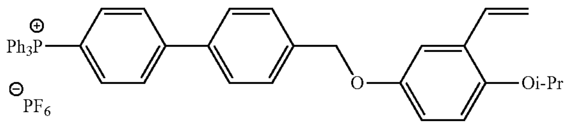

To a mixture of the phosphonium salt (13) (but the $PF_6$ salt) (1.7 g, 2.9 mmol, 1.0 equiv), 4-isopropoxy-3-vinyl-phenol (640 mg, 3.6 mmol, 1.2 equiv), triphenylphosphine (940 mg, 3.6, 1.2 equiv) and $CH_2Cl_2$ (30 mL, 0.1 M) at −5° C. was added DEAD (570 μL, 3.6 mmol, 1.2 equiv) dropwise during 10 min. After 1 h at room temperature the mixture was concentrated under reduced pressure. The crude product was diluted with $CH_2Cl_2$ (4 ml) and was precipitated with $Et_2O$ (50 mL). This operation was repeated twice. The residue was purified by flash chromatography (MeOH/$CH_2Cl_2$, 0:100-5:95) to afford pure phosphonium salt (14) (1.75 g, 80%) as a solid foam, which has been characterized has follows:

$^{13}$C NMR (100 MHz, $CDCl_3$) δ 152.8 (s), 149.6 (s), 147.6 (s), 138.4 (s), 137.7 (s), 135.6 (s), 134.9 (d, J=10.7 Hz), 134.3 (d, J=10.3 Hz), 131.6 (s), 130.7 (d, J=12.8 Hz), 129.0 (s), 128.9 (d, J=13.2 Hz), 128.1 (s), 127.6 (s), 117.5 (d, J=89.1 Hz), 116.8 (s), 115.5 (d, J=90.7 Hz), 114.9 (s), 114.2 (s), 112.3 (s), 72.1 (s), 69.9 (s), 22.1 (s).

$^{31}$P (162 MHz, $CDCl_3$) δ 23.1, −143.9 (sept, J=713 Hz).

LRMS (APCI, Pos) calcd for $C_{42}H_{38}O_2P$ $[M]^+$: 605.7 m/z, observed 605.2.

10

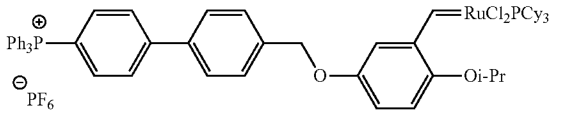

A mixture of phosphonium (14) (225 mg, 0.30 mmol, 1.0 equiv), Grubbs first generation catalyst ($Cl_2Ru(PCy_3)$ =CHPh) (305 mg, 0.36 mmol, 1.2 equiv), CuCl (27 mg, 0.27, 0.9 equiv) and $CH_2Cl_2$ (15 mL, 0.02 M) were heated under reflux for 2 h under argon. The mixture was concentrated under reduced pressure. The crude product was diluted with $CH_2Cl_2$ (2.5 ml) and was precipitated with $Et_2O$ (20 mL). This operation was repeated four times to afford pure catalyst (10) (350 mg, 97%) as a solid green foam, has been characterized has follows:

$^1H$ NMR (400 MHz, $CDCl_3$) δ17.38 (d, J=4.5 Hz, 1H), 7.95 (dd, J=3.1, 8.4 Hz, 2H), 7.89-7.85 (m, 3H), 7.78-7.74 (m, 6H), 7.71-7.87 (m, 10H), 7.58 (d, J=8.2 Hz, 2H), 7.33 (d, J=2.9 Hz, 1H), 7.28 (dd, J=2.9, 8.9 Hz, 1H), 6.99 (d, J=8.9 Hz, 1H), 5.19 (sept, J=6.1 Hz, 1H), 5.16 (s, 2H), 2.33 (br q, J=12.1 Hz, 3H), 2.12-2.07 (m, 6H), 1.92-1.81 (m, 12H), 1.77 (d, J=6.1 Hz, 6H), 1.73-1.68 (m, 3H), 1.29-1.25 (m, 9H). $^{13}C$ NMR (100 MHz, $CDCl_3$) δ 278.6 (s), 154.0 (s), 147.5 (d, J=2.8 Hz), 147.1 (s), 143.9 (s), 138.0 (s), 137.6 (s), 135.4 (d, J=3.1 Hz), 134.7 (d, J=10.5 Hz), 134.1 (d, J=10.2 Hz), 130.5 (d, J=12.8 Hz), 128.8 (d, J=13.1 Hz), 128.0 (s), 127.5 (s), 117.3 (d, J=89.0 Hz), 116.1 (s), 115.4 (d, J=90.6 Hz), 113.7 (s), 75.3 (s), 70.2 (s), 35.3 (d, J=24.7 Hz), 29.9 (s), 27.5 (d, J=10.3 Hz), 26.1 (s), 21.8 (s). $^{31}P$ (162 MHz, $CDCl_3$) δ 58.7, 23.1, −143.9 (sept, J=713 Hz).

EXAMPLE 6

Use of Phosphonium Supported Ruthenium Catalyst (10) in a Ring Closing Metathesis Reaction and Recovery and of the Catalyst for Further Uses

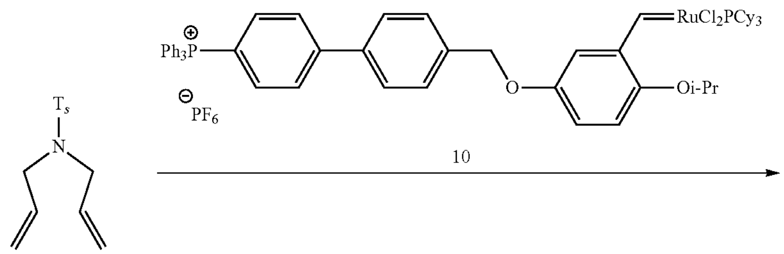

A solution of N,N-Diallyl-4-methyl-benzenesulfonamide (251 mg, 1.0 mmol, 1.0 equiv), phosphonium catalyst (10) (30 mg, 0.025 mmol, 0.025 equiv) in $CH_2Cl_2$ (20 mL, 0.05 M) were heated under reflux for 3 h under argon. The mixture was concentrated under reduced pressure. The crude product was diluted with $CH_2Cl_2$ (1 ml) and the catalyst was precipitated with $Et_2O$ (10 mL). Filtration produced the phosphonium catalyst (10) in quantitative yield (85% purity). Evaporation of the filtrate afforded pure 1-(toluene-4-sulfonyl)-2,5-dihydro-1H-pyrrole (99.5%). Second cycle: 1-(toluene-4-sulfonyl)-2,5-dihydro-1H-pyrrole was obtained in 98% yield and the phosphonium catalyst (10) could be recovered in quantitative yield in 83% purity.

Third cycle: 1-(toluene-4-sulfonyl)-2,5-dihydro-1H-pyrrole was obtained in 97% yield and the phosphonium catalyst (10) could be recovered in quantitative yield in 77% purity. Fourth cycle: 1-(toluene-4-sulfonyl)-2,5-dihydro-1H-pyrrole was obtained in 97% yield and the phosphonium catalyst (10) could be recovered in quantitative yield in 68% purity. Fifth cycle: 1-(toluene-4-sulfonyl)-2,5-dihydro-1H-pyrrole was obtained in 95% yield and the phosphonium catalyst (10) could be recovered in quantitative yield in 67% purity.

EXAMPLE 7

Phosphonium Supported Tin Chloride Reagent (15)

15

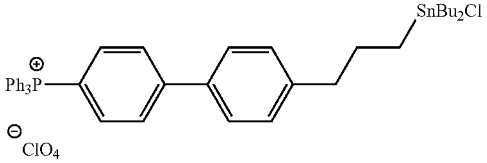

Preparation of the phosphonium supported tin chloride reagent (15) was carried out through synthesis of intermediates compounds (16) and (17).

16

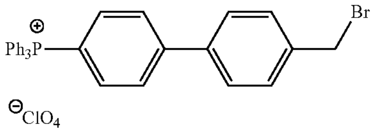

To 4-(4'-hydroxymethyl)biphenyl triphenylphosphonium perchlorate (13) (11.9 g, 21.8 mmol, 1.0 equiv) in DMF (100 mL, 0.2 M) was added $CBr_4$ (10.9 g, 33.0 mmol, 1.5 equiv) and $PPh_3$ (8.9 g, 33 mmol, 1.5 equiv). After 15 min, the solution was heated to 60° C. for 3 h. The brown solution was cooled to room temperature, and diluted with $CH_2Cl_2$ (600 ml). The organic layer was washed ten times with water (100 mL). The organic solution was dried over anhydrous $MgSO_4$ and was concentrated under reduced pressure. The crude product was diluted with $CH_2Cl_2$ (25 ml) and was precipitated with $Et_2O$ (200 mL). This procedure was repeated three times and the product was finally purified by flash chromatography ($MeOH/CH_2Cl_2$ 0:100-1:99) to afford pure 4-(4-bromomethylphenyl)phenyl triphenylphosphonium perchlorate (16) (11.1 g, 84%) as a solid foam, which was characterized as follows:

mp 72-76° C.

$^{1}$H NMR (400 MHz, $CDCl_3$) δ 7.95-7.87 (m, 2H), 7.87-7.78 (m, 2H), 7.78-7.69 (m, 6H), 7.69-7.53 (m, 11H), 7.46 (d, J=7.8 Hz, 2H), 4.49 (s, 2H). $^{13}$C NMR (100 MHz, $CDCl_3$) δ 147.4 (s), 138.8 (s), 138.3 (s), 135.6 (d, J=2.6 Hz), 135.0 (d, J=10.7 Hz), 134.4 (d, J=10.2 Hz), 130.7 (d, J=12.9 Hz), 130.0 (s), 129.1 (d, J=13.3 Hz), 128.0 (s), 117.5 (d, J=89.2 Hz), 115.8 (d, J=90.8 Hz), 33.0 (s). $^{31}$P (162 MHz, $CDCl_3$) δ 23.1. IR (film) 3026, 1595, 1437, 1337, 1267, 1079 (Cl═O) $cm^{-1}$.

LRMS (APCI, Pos) calcd for $C_{31}H_{25}{}^{79}Br_1P_1$ $[M]^+$: 507.1 m/z, observed 507.0; $C_{31}H_{25}{}^{81}Br_1P_1$ $[M]^+$: 509.1 m/z, observed 509.0. LRMS (APCI, Neg) calcd for $^{35}ClO_4$ $[M]^-$: 99.0 m/z, observed 99.1; $^{37}ClO_4$ $[M]^-$: 101.0 m/z, observed 101.1.

17

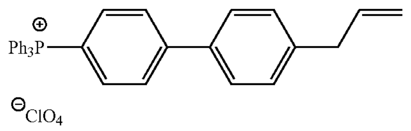

To compound (16) (10.4 g, 17.1 mmol, 1.0 equiv) and CuI (330 mg, 1.7 mmol, 0.1 equiv) in $CH_2Cl_2$ (70 mL, 0.25 M) at −78° C. was added vinylmagnesium bromide (1.0 M in THF, 19 mL, 19.0 mmol, 1.1 equiv). The mixture which was protected from light, was warmed to 0° C. for 30 min and to room temperature for 20 h. A saturated aqueous $NH_4Cl$ (50 mL) was added. The aqueous layer was washed with $CH_2Cl_2$ (100 mL). The organic layer was washed with water (50 mL), dried over anhydrous $MgSO_4$ and concentrated under reduced pressure. The crude product was purified by flash chromatography (MeOH/$CH_2Cl_2$ 0:100-4:96) to afford pure (17) (8.4 g, 86%) as a solid foam, which was characterized as follows:

mp 74-81° C.

$^{1}$H NMR (400 MHz, $CDCl_3$) δ7.94-7.90 (m, 2H), 7.86-7.82 (m, 2H), 7.77-7.71 (m, 6H), 7.66-7.57 (m, 11H), 7.28 (d, J=8.0 Hz, 2H), 5.94-5.89 (m, 1H), 5.09-5.03 (2m, 2H), 3.39 (d, J=8.7 Hz, 2H). $^{13}$C NMR (100 MHz, $CDCl_3$) δ 148.0 (d, J=3.1 Hz), 141.4 (s), 136.8 (s), 136.0 (s), 135.7 (d, J=2.5 Hz), 134.9 (d, J=10.6 Hz), 134.3 (d, J=10.3 Hz), 130.7 (d, J=12.8 Hz), 129.5 (s), 128.8 (d, J=13.3 Hz), 127.5 (s), 117.6 (d, J=89.1 Hz), 116.3 (s), 115.1 (d, J=91.1 Hz), 39.8 (s). $^{31}$P (162 MHz, $CDCl_3$) δ 23.1. IR (film) 3060, 1595, 1437, 1267, 1079 (Cl═O) $cm^{-1}$. LRMS (APCI, Pos) calcd for $C_{33}H_{28}P_1$ $[M]^+$: 455.2 m/z, observed 455.0. LRMS (APCI, Neg) calcd for $^{35}ClO_4$ $[M]^-$: 99.0 m/z, observed 99.1; $^{37}ClO_4$ $[M]^-$: 101.0 m/z, observed 101.0.

15

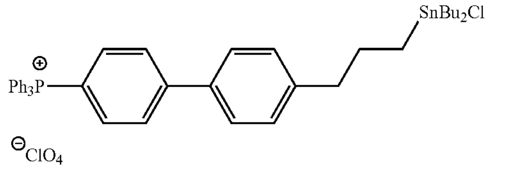

To a solution of (17) (7.3 g, 13.3 mmol, 1.0 equiv) and $Bu_2SnCl_2$ (10.0 g, 33.0 mmol, 2.5 equiv) in a mixture of $CH_3CN$ (7 mL) and benzene (15 mL) under argon was added $Bu_2SnH_2$ (6.5 mL, 33 mmol, 2.5 equiv). The solution was irradiated with a sun lamp for 10 h. $CH_3CN$ (350 mL, degassed under argon) and hexane (100 mL, degassed under argon) were added to the solution. The $CH_3CN$ layer was washed twice with hexane (100 mL, degassed under Ar) and concentrated under reduced pressure. The crude product was dissolved in $CH_2Cl_2$ (25 ml) and precipitated by adding $Et_2O$ (200 mL). This process was repeated three times to afford pure (15) (9.8 g, 90%) as a solid foam, which was characterized as follows:

mp 57-63° C.

$^{1}$H NMR (400 MHz, $CDCl_3$) δ 7.87-7.84 (m, 2H), 7.84-7.72 (m, 2H), 7.71-7.68 (m, 6H), 7.60-7.51 (m, 11H), 7.23 (d, J=7.7 Hz, 2H), 2.62 (br t, J=7.4 Hz, 2H), 1.98-1.92 (m, 1H), 1.62-1.52 (m, 4H), 1.35-1.19 (m, 10H), 0.79 (t, J=7.3 Hz, 6H). $^{13}$C NMR (100 MHz, $CDCl_3$) δ 148.0 (d, $J_{C—P}$=2.7 Hz), 143.3 (s), 135.6 (d, $J_{C—P}$=2.0 Hz), 135.5 (s), 134.8 (d, $J_{C—P}$=10.6 Hz), 134.2 (d, $J_{C—P}$=10.3 Hz), 130.6 (d, $J_{C—P}$=12.8 Hz), 129.3 (s), 128.6 (d, $J_{C—P}$=13.1 Hz), 127.3 (s), 117.5 (d, $J_{C—P}$=89.1 Hz), 114.9 (d, $J_{C—P}$=91.0 Hz), 39.4 (s and d, $J_{C—Sn}$=67.6 Hz), 27.7 (s and d, $J_{C—Sn}$=24.8 Hz), 27.5 (s and d, $J_{C—Sn}$=23.2 Hz), 26.6 (s and d, $J_{C—Sn}$=66.8 Hz), 18.2 (s and 2d, $J_{C\text{-}117Sn}$=339 Hz and $J\text{-}_{C\text{-}119Sn}$=352 Hz), 17.8 (s and 2d, $J_{C\text{-}117Sn}$=327 Hz and $J_{C\text{-}119Sn}$=342 Hz), 13.6 (s). $^{31}$P (162 MHz, $CDCl_3$) δ 23.1. IR (film) 2954, 1595, 1437, 1275, 1088 (Cl═O) $cm^{-1}$. LRMS (APCI, Pos) calcd for $C_{41}H_{47}{}^{35}ClP^{120}Sn$ $[M]^+$: 725.0 m/z, observed 725.1. LRMS (APCI, Neg) calcd for $^{35}ClO_4$ $[M]^-$: 99.0 m/z, observed 99.0; $^{37}ClO_4$ $[M]^-$: 101.0 m/z, observed 101.0.

EXAMPLE 8

Use of the Phosphonium Supported Tin Chloride Reagent (15) as a Dehalogenating Agent

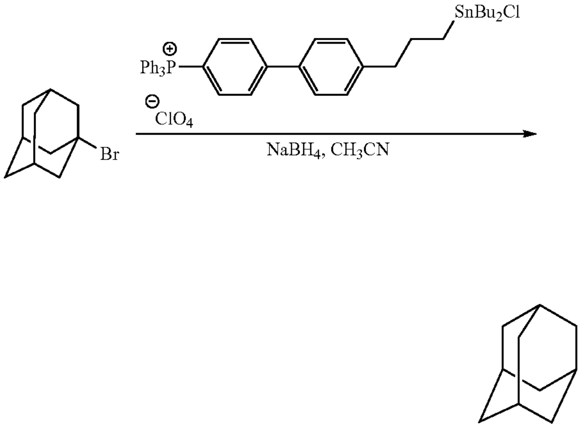

A solution of 1-bromoadamantane (108 mg, 0.5 mmol, 1.0 equiv), the phosphonium supported chlorostanne (15) (82 mg, 0.1 mmol, 0.2 equiv), $NaBH_4$ (28 mg, 0.75 mmol, 1.5 equiv) in $CH_3CN$ (2.5 mL, 0.2 M) was heated to reflux under Ar for 10 min. Then AIBN (8 mg, 0.05 mmol, 0.1 equiv) was added and the solution was heated to reflux for an additional 2 h. $CHCl_3$ (5 mL) was added and the solution was filtered through Celite and the filtrate was concentrated under reduced pressure. The crude product was diluted with $CHCl_3$ (1 ml) and the tin residues were precipitated by adding $Et_2O$ (10 mL). The mixture was filtered through Celite and the filtrate was evaporated to afford pure adamantane in quantitative yield. No traces (<1%) of stannane impurities could be detected by NMR.

EXAMPLE 9

Phosphonium Supported Carbodiimide Reagent or Scavenger (18)

18

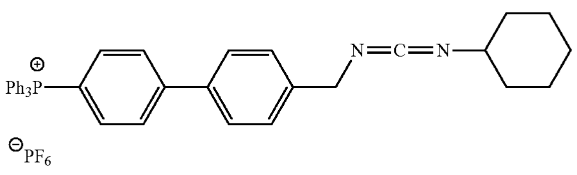

Preparation of the supported carbodiimide reagent or scavenger (18) was carried out through synthesis of intermediate compound (19).

19

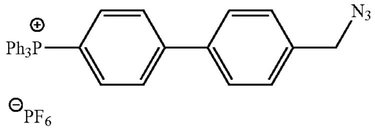

As described above, to a solution of phosphonium supported benzyl alcohol (13) (but the $PF_6$ salt) (17 g) in DMF was added triphenylphosphine (1.5 equiv) and $CBr_4$ (1.5 equiv). The mixture was stirred for 15 min at rt and $NaN_3$ (1.5 equiv) was then added. The reaction mixture was heated for 5 min at rt and 3 h at 60° C. Dichloromethane (700 mL) and $H_2O$ (200 mL) were added. The layers were separated and the aqueous layer was washed with $CH_2Cl_2$ (100 mL). The combined organic layers were washed with $H_2O$ (10×100 mL), dried over $MgSO_4$, and concentrated under reduced pressure to afford the corresponding azide (19) (20 g). Purification by flash chromatography afforded the desired compound in 90% yield, which was characterized as follows:

$^{1}H$ NMR (400 MHz, $CDCl_3$) δ 8.12-8.05 (m, 2H), 7.93-7.84 (m, 2H), 7.84-7.74 (m, 6H), 7.73-7.62 (m, 11H), 7.45 (d, J=7.9 Hz, 2H), 4.40 (s, 2H).

$^{13}C$ NMR (100 MHz, $CDCl_3$) 147.8 (s), 138.4 (s), 136.7 (s), 135.9 (d, J=2.7 Hz), 135.1 (d, J=10.7 Hz), 134.5 (d, J=10.3 Hz), 130.8 (d, J=12.8 Hz), 129.3 (d, J=12.8 Hz), 129.2 (s), 128.1 (s), 117.7 (d, J=89.0 Hz), 115.9 (d, J=90.8 Hz), 54.4.0 (s).

$^{31}P$ (162 MHz, $CDCl_3$) 23.1, −143.9 (sept, J=713 Hz).

IR (film) 2083, 1597, 1438, 1108, 827 (P—F) $cm^{-1}$.

LRMS (APCI, Pos) calcd for $C_{31}H_{25}N_3P_1$ $[M]^+$: 470.2 m/z, observed 470.1.

LRMS (APCI, Neg) calcd for $PF_6$ $[M]^-$: 145.0 m/z, observed 145.0.

18

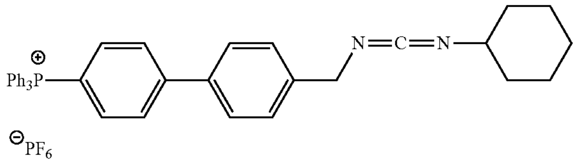

To a solution of the azide (19) (2.09 g, 3.00 mmol) in $CH_2Cl_2$ (14 mL) was added triphenylphosphine (1.5 equiv). After the addition, cyclohexylisocyanate (1.5 equiv) was added dropwise. The mixture was stirred at rt for 30 min and at 50° C. for 9 h. The mixture was cooled to rt and $Et_2O$ was added to precipitate the carbodiimide. Filtration afforded the desired reagent that was purified by repeating this solubilization ($CH_2Cl_2$)-precipitation ($Et_2O$) procedure four times. Drying of the solid led to the desired carbodiimide reagent (18) as a solid (2.17 g, 96%), which was characterized as follows:

$^{1}H$ NMR (400 MHz, $CDCl_3$) 8.20-8.10 (m, 2H), 7.89-7.85 (m, 2H), 7.75-7.63 (m, 17H), 7.44 (d, J=7.9 Hz, 2H), 4.28 (s, 2H), 3.21-3.11 (m, 1H), 1.74-1.72 (m, 2H), 1.58-1.56 (m, 2H), 1.43-1.45 (m, 1H), 1.16-0.86 (m, 5H).

$^{13}C$ NMR (100 MHz, $CDCl_3$) 147.6 (s), 140.2 (s), 139.7 (s), 137.3 (s), 135.5 (d, J=2.5 Hz), 134.8 (d, J=10.7 Hz), 134.2 (d, J=10.3 Hz), 130.5 (d, J=12.8 Hz), 128.8 (d, J=13.2 Hz), 128.3 (s), 127.6 (s), 117.4 (d, J=89.1 Hz), 115.4 (d, J=90.9 Hz), 55.5 (s), 50.1 (s), 34.6 (s), 25.2 (s), 24.2 (s).

EXAMPLE 10

Phosphonium Supported Amine Scavenger (20)

20

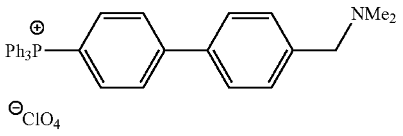

To a solution of (12) (0.136 g, 0.25 mmol) in 0.5 mL of 1,2-dichloroethane was added dimethylamine (0.187 mL, 1.5 equiv) followed by $NaBH(OAc)_3$ (74 mg, 1.4 equiv). After the addition, the solution was stirred at room temperature for 6 h. The solution was washed with 2 mL of $NaHCO_3$. To the organic layer was added 3 mL of MeCN and $LiClO_4.3H_2O$ (48 mg, 0.3 mmol) and then the mixture was concentrated. The residue obtained was dissolved in 10 mL $CH_2Cl_2$. The $CH_2Cl_2$ solution was washed with 2 mL of $H_2O$ and dried over $MgSO_4$. Removal of solvent gave the product (20) as a yellow-white glassy solid, which was characterized as follows:

$^{1}H$ NMR (400 MHz, $CDCl_3$) 8.14-8.04 (m, 2H), 7.98-7.87 (m, 2H), 7.78-7.75 (m, 6H), 7.67-7.61 (m, 11H), 7.45 (d, J=7.9 Hz, 2H), 3.50 (s, 2H), 2.28 (s, 6H).

$^{13}C$ NMR (100 MHz, $CDCl_3$) 147.8 (s), 139.8 (s), 136.9 (s), 135.6 (d, J=2.5 Hz), 134.8 (d, J=10.7 Hz), 134.2 (d, J=10.3 Hz), 130.5 (d, J=12.9 Hz), 129.8 (s), 128.8 (d, J=13.2 Hz), 127.3 (s), 117.4 (d, J=89.1 Hz), 115.2 (d, J=91.0 Hz), 63.5 (s), 45.1 (s).

$^{31}P$ (162 MHz, $CDCl_3$) 23.1.

IR (film) 2769, 1596, 1437, 1080 (Cl═O) $cm^{-1}$.

LRMS (APCI, Pos) calcd for $C_{33}H_{31}N_1P_1$ $[M]^+$: 472.2 m/z, observed 472.1.

EXAMPLE 11

Use of the Phosphonium Supported Amine (20) as an Acid Scavenger

To a solution of the phosphonium supported amine perchlorate in $CH_2Cl_2$ was added 1 equivalent of camphorsulfonic acid. Addition of ether, followed by filtration led to a filtrate that did not contain any camphorsulfonic acid by NMR (<1%).

EXAMPLE 12

Phosphonium Supported Peptide Synthesis

21

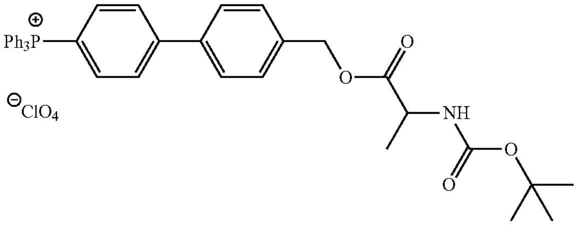

In an inert atmosphere of argon, compound (13) (1.9 g, 3.48 mmol), (L)-Boc-Ala-OH (989 mg, 5.22 mmol), and DMAP (85 mg, 0.69 mmol) were suspended in $CH_2Cl_2$ (7 ml). The resulting reaction mixture was cooled to 0° C., and EDCI (1 g, 5.22 mmol) was added. After 1 h at 0° C., the reaction mixture was allowed to warm at r.t., and stirred for 3 h. The reaction vessel was quenched with $H_2O$ (20 ml), and extracted with $CH_2Cl_2$ (2×30 ml). The organics were washed with $H_2O$ (2×50 ml), brine (2×50 ml), dried ($Na_2SO_4$), and concentrated in vacuo to afford a pale yellow residue. Treatment with $CH_2Cl_2/Et_2O$ led to the desired compound (21), which was sufficiently pure to be used in the next step (2.30 g, 92%). The compound (21) was characterized as follows:

$^1$H-NMR (400 MHz, $CDCl_3$): 7.96-7.87 (m, CH-arom., 4 H), 7.80-7.64 (m, CH-arom., 17 H), 7.43 (d, J=8.08, CH-arom., 2 H), 5.14 (d, J=7.96, $OCH_2$, 2 H), 4.99 (br. s., NH, 1 H), 4.26 (br. q, CH-aliph., 1 H), 1.41 (s, $CH_3$, 9 H), 1.38 (br. s, $CH_3$, 3 H). $^{13}$C-NMR (50 MHz, $CDCl_3$): 173.60, 155.56, 148.11, 138.67, 137.06, 137.17 (d, J=1.35), 135.43 (d, J=5.30), 134.83 (d, J=5.15), 131.20 (d, J=6.40), 129.53 (d, J=6.60), 129.28, 128.19, 117.96 (d, J=44.55), 116.15 (d, J=45.45), 80.30, 66.75, 49.72, 28.72, 18.95. $^{31}$P-NMR (162 MHz, $CDCl_3$): 24.14 (s).

22

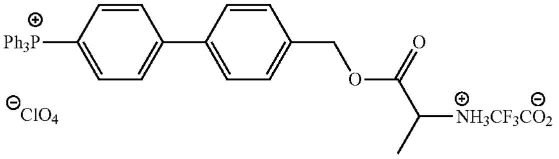

Compound (21) (150 mg, 0.21 mmol) was dissolved in $CH_2Cl_2$ (1.8 ml), and TFA (0.2 ml) was slowly added. The resulting reaction mixture was stirred at rt for 0.5 h, and $Et_2O$ (10 ml) was added in order to precipitate the phosphonium salt. The $Et_2O$ phase was decanted, and the pale yellow residue was taken up with $CH_2Cl_2$. Treatment with $Et_2O$ (2×) afforded the target compound (22) as a pale yellow residue (152 mg, quant.), which was characterized as follows:

$^1$H-NMR (400 MHz, $CD_2Cl_2$): δ 8.13 (br. s., $NH_3^+$, 3 H), 7.99-7.92 (m, CH-arom., 5 H), 7.81-7.65 (m, CH-arom., 16 H), 7.44 (d, J=8.04, CH-arom., 2 H), 5.29 (br. s, $OCH_2$, 2 H), 4.07 (br. q., CH-aliph., 1 H), 1.68 (br. d., $CH_3$, 3 H).

23

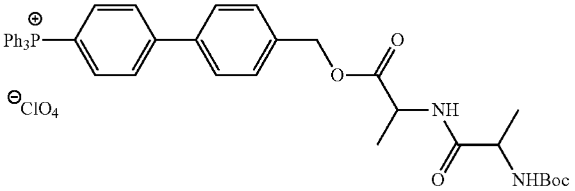

In an inert atmosphere of argon, compound (22) (900 mg, 1.23 mmol), (L)-Boc-Ala-OH (466 mg, 2.46 mmol), HOBt (332 mg, 2.46 mmol), and Hünig's base (850 μl, 4.92 mmol) were suspended in $CH_2Cl_2$ (2.5 ml). The resulting reaction mixture was stirred at r.t. for 0.5 h, and then cooled to 0° C. DCC (507 mg, 2.46 mmol) was added, the reaction stirred at 0° C. for 1 h, and then allowed to warm at r.t. After 22 h, the generated white precipitate was filtered off, and washed with $CH_2Cl_2$ (20 ml). The organic phase was washed with $H_2O$ (2×20 ml), brine (2×20 ml), dried ($Na_2SO_4$), and concentrated in vacuo to afford a pale yellow residue. Treatment with $CH_2Cl_2/Et_2O$ gave rise to compound (23) as a pale yellow residue, which was sufficiently pure to be used in the next step (900 mg, 93%). The compound (23) has been characterized has follows:

$^1$H-NMR (400 MHz, $CDCl_3$): δ 7.92-7.83 (m, CH-arom., 5 H), 7.76-7.60 (m, CH-arom., 16 H), 7.42 (d, J=7.96, CH-arom., 2 H), 5.30 (br. s., NH, 2 H), 5.15 (br. s., $OCH_2$, 2 H), 4.06 (br. q, CH-aliph., 2 H), 1.39 (s, $CH_3$, 9 H), 1.29 (d, J=7.04, $CH_3$, 3 H). $^{13}$C-NMR (50 MHz, $CDCl_3$): δ 173.02, 172.87, 155.38, 148.11, 138.56, 137.09, 136.14 (d, J=1.30), 135.38 (d, J=5.30), 134.79 (d, J=5.15), 131.17 (d, J=6.45), 129.48 (d, J=6.60), 129.21, 128.13, 117.98 (d, J=44.55), 116.14 (d, J=41.65), 80.21, 66.71, 48.60, 28.67, 18.30. $^{31}$P-NMR (162 MHz, $CDCl_3$): δ 24.11 (s).

24

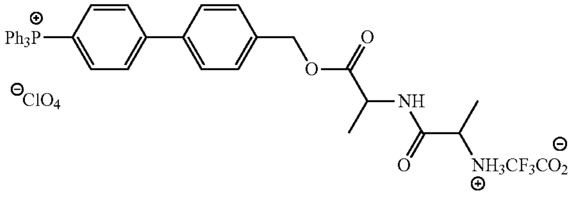

Compound (23) (755 mg, 0.95 mmol) was dissolved in $CH_2Cl_2$ (8 ml), cooled to 0° C., and TFA (2 ml) was slowly added. The resulting reaction mixture was stirred at 0° C. for 15 min, and then 2 h at r.t., followed by the addition of $Et_2O$ (30 ml) in order to precipitate the phosphonium salt.

The $Et_2O$ phase was decanted, and the pale yellow residue was taken up with $CH_2Cl_2$ (just a few amount). Treatment with $Et_2O$ (2×) afforded the target compound (24) as a pale yellow residue (765 mg, quant.). The compound (24) was characterized as follows:

$^1H$-NMR (400 MHz, $CD_2Cl_2$): δ 8.04 (br. s, $NH_3^+$, 3 H), 7.99-7.91 (m, CH-arom., 5 H), 7.80-7.65 (m, CH-arom., 16 H), 7.49 (d, J=8.08, CH-arom., 2 H), 5.22-5.15 (dd, $J_1$=12.68, $J_2$=12.72, $OCH_2$, 2H), 4.51 (br. q, CH-aliph., 2 H), 1.41 (br. d, $CH_3$, 6 H).

EXAMPLE 13

Cleavage of an Amino Acid from the Phosphonium Support

25

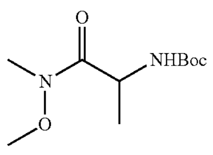

In an inert atmosphere of argon, the phosphonium supported N-BocAla (21) (500 mg, 0.68 mmol) and Me(MeO)NH.HCl (100 mg, 1.02 mmol) were suspended in THF (4 ml). The resulting mixture was cooled to −20° C., and i-PrMgCl (2 M in THF, 1.5 ml, 2.73 mmol) was added drop-wise. At that point, the colorless solution turned to yellow. The reaction mixture was stirred at −20° C. for 1.5 h, quenched with a sat. aq. soln. of $NH_4Cl$ (10 ml), and extracted with $CH_2Cl_2$ (2×30 ml).

The combined organic phases were washed with $H_2O$ (2×60 ml), brine (2×60 ml), dried ($Na_2SO_4$), and concentrated in vacuo to afford a white foam. This white foam was taken up with $CH_2Cl_2$ (just a few amount), and washed with $Et_2O$ (50 ml). This operation was done twice. The $Et_2O$ phase was concentrated, affording compound (25) as a white residue, which was sufficiently pure (>95%) (130 mg, 81%). The compound (25) has been characterized as follows:

$^1H$-NMR (400 MHz, $CDCl_3$): δ 5.27 (d, J=8.76, NH, 1 H), 4.63 (br. t, CH-alipha., 1 H), 3.68 (s, $OCH_3$, 3 H), 3.13 (s, $CH_3$, 3 H), 1.35 (s, $CH_3$, 9 H), 1.26 (d, J=6.92, $CH_3$, 3 H). $^{13}C$-NMR (50 MHz, $CDCl_3$): 174.02, 155.55, 79.82, 61.97, 46.88, 32.51, 28.72, 18.99.

EXAMPLE 14

Phosphonium Supported Peptide Synthesis

The synthesis of compound (37) is subsequently described.

In an inert atmosphere of Argon, compound (37) (868 mg, 1.33 mmol), (L)-Fmoc-Ala-OH (621 mg, 1.99 mmol), and DMAP (33 mg, 0.26 mmol) were suspended in $CH_2Cl_2$ (2.7 ml). The resulting white suspension was cooled to 0° C., and EDCI (382 mg, 1.99 mmol) was added. The reaction mixture was stirred at 0° C. for 1 h, and then at r.t. for 2 h. The white suspension was filtered off, and washed with $CH_2Cl_2$ (20 ml). The organic phase was washed with $H_2O$ (2×30 ml), HCl 5% (1×30 ml), brine (2×30 ml), dried ($MgSO_4$), and concentrated in vacuo to afford the target compound (27) as a white foam. Treatment with $CH_2Cl_2/Et_2O$ led to a white foam (1 g, 86%). The compound (27) was characterized as follows:

$R_f$=0.3 ($CH_2Cl_2$/MeOH, 19:1).

$^1H$-NMR (400 MHz, $CDCl_3$): 7.92 (d, J=5.56, CH-arom., 2 H), 7.87-7.83 (m, CH-arom, 4 H), 7.74-7.60 (m, CH-arom., 16 H), 7.56 (s, CH-arom., 2 H), 7.51 (d, J=7.64, CH-arom., 2 H), 7.35 (t, $J_1$=7.24, $J_2$=7.36, CH-arom., 2 H), 7.25 (br. s, CH-arom., 5 H), 6.91 (d, J=7.92, CH-arom., 2 H), 5.58 (d, J=7.44, NH, 1 H), 5.07 (s, $OCH_2$, 2 H), 5.04 (s, $OCH_2$, 2 H), 4.38-4.23 (m, $OCH_2$, CH-aliph. 4 H), 1.41 (d, J=6.84, $CH_3$, 3 H).

Dept135 (50 MHz, $CDCl_3$): 136.17 (d, J=1.15, CH-arom., 3 H), 135.41 (d, J=5.30, CH-arom., 2 H), 134.81 (d, J=5.10, CH-arom., 6 H), 131.19 (d, J=6.40, CH-arom., CH-arom., 6 H), 130.53 (s, CH-arom., 2 H), 129.46 (d, J=6.60, CH-arom., 2 H), 128.63 (s, CH-arom., 2 H), 128.17 (s, CH-arom., 2 H), 127.55 (s, CH-arom., 2 H), 120.39 (s, CH-arom., 4 H), 115.31 (s, CH-arom., 4 H), 69.81 (s, $OCH_2$, 2 H), 67.34 (s, $OCH_2$, 4 H), 50.24 (s, CH-aliph., 1 H), 47.46 (s, CH-aliph., 1 H), 18.84 (s, $CH_3$, 3 H).

$^{13}C$-NMR (50 MHz, $CDCl_3$): 173.34, 159.12, 156.17, 148.17, 144.25 (d, J=9.75), 141.63, 138.45, 138.26, 136.17 (d, J=1.15), 135.41 (d, J=5.35), 134.81 (d, J=5.10), 131.19 (d, J=6.45), 130.52, 129.46 (d, J=6.60), 128.63, 128.30, 128.17, 127.55, 120.39, 117.97 (d, J=44.55), 116.00 (d, J=45.30), 115.31, 69.81, 67.34, 50.25, 47.46, 18.84.

$^{31}P$-NMR (162 MHz, $CDCl_3$): 24.07 (s).

37

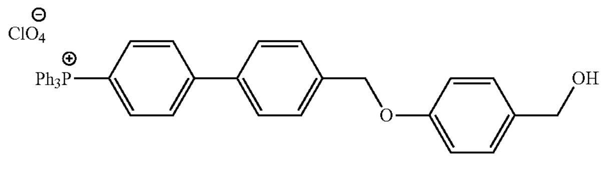

27

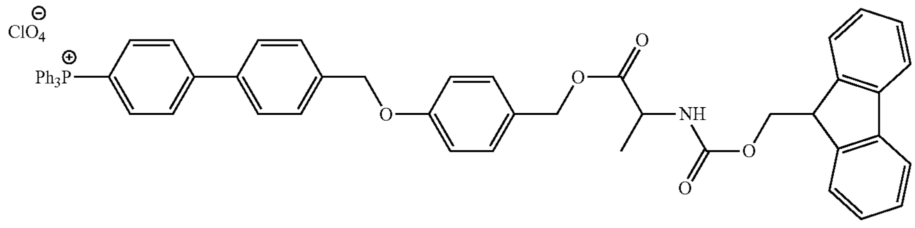

28

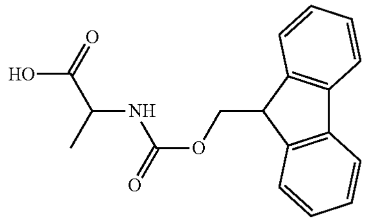

Compound (27) (200 mg, 0.21 mmol) was dissolved in $CH_2Cl_2$ (0.8 ml), and cooled to 0° C. TFA (0.2 ml) was slowly added, and the resulting purple solution stirred at 0° C. for 1.5 h. The reaction vessel was concentrated in vacuo, and the resulting residue taken up with $CH_2Cl_2$ (just a few amount). The organic was treated with $Et_2O$ (2×50 ml), and the $Et_2O$ phases were combined, washed with a 10% aq. soln. of pyridine (100 ml), a 10% aq. soln. of HCl (2×100 ml), $H_2O$ (2×100 ml), brine (2×100 ml), dried ($Na_2SO_4$), and concentrated in vacuo affording the target compound (28) as a white residue (40 mg, 61%). The compound was compared with an authentic sample, and was in agreement.

29

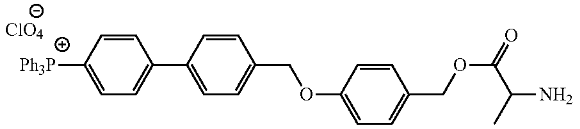

Compound (27) (455 mg, 0.48 mmol) was dissolved in DMF (4 ml), and piperidine (1 ml) was added. The reaction mixture was stirred at r.t. for 1 h, and diluted with $CH_2Cl_2$ (20 ml). The organic phase was washed with $H_2O$ (2×30 ml), brine (2×30 ml), dried ($Na_2SO_4$), and concentrated in vacuo to afford a white foam. Treatment with $CH_2Cl_2/Et_2O$ led to the desired compound (29) as a white foam (345 mg, quant.). The compound (29) was characterized as follows:

$R_f$=0.2 ($CH_2Cl_2$/MeOH, 19:1).

$^1$H-NMR (400 MHz, $CDCl_3$): 7.93 (d, J=5.72, CH-arom., 2 H), 7.84 (d, J=7.04, CH-arom., 3 H), 7.75 (br. s, CH-arom., 6 H), 7.70-7.61 (m, CH-arom., 10 H), 7.52 (d, J=7.16, CH-arom., 2 H), 7.26 (d, J=7.48, CH-arom., 2 H), 6.94 (d, J=7.60, CH-arom., 2 H), 5.09 (s, $OCH_2$, 2 H), 5.04 (s, $OCH_2$, 2 H), 1.60 (br. s, $NH_2$, 2 H), 1.28 (d, J=6.64, $CH_3$, 3 H).

Dept135 (50 MHz, $CDCl_3$): 136.15 (d, J=1.00, CH-arom., 3 H), 135.41 (d, J=5.30, CH-arom., 2 H), 134.81 (d, J=5.15, CH-arom., 6 H), 131.18 (d, J=6.40, CH-arom., 6 H), 130.47 (s, CH-arom., 2 H), 129.47 (d, J=6.60, CH-arom., 2 H), 128.59 (s, CH-arom., 2 H), 128.17 (s, CH-arom., 2 H), 115.33 (s, CH-arom., 2 H), 69.88 (s, $OCH_2$, 2 H), 66.77 (s, $OCH_2$, 2 H), 50.49 (s, CH-aliph., 1 H), 21.05 (s, $CH_3$, 3 H).

In an inert atmosphere of Argon, compound (29) (120 mg, 0.16 mmol), (L)-Fmoc-Ala-OH (110 mg, 0.33 mmol), HOBt (45 mg, 0.33 mmol), and Hünig's base (115 μl, 0.60 mmol) were suspended in $CH_2Cl_2$ (1 ml). The reaction mixture was cooled to 0° C., and DCC (69 mg, 0.33 mmol) was added. The resulting suspension was stirred at 0° C. for 1 h, and then allowed to warm at r.t. After 20 h, the reaction vessel was filtered off, and washed with $CH_2Cl_2$ (10 ml). The organics were washed with $H_2O$ (2×30 ml), brine (2×30 ml), dried ($Na_2SO_4$), and concentrated in vacuo. Treatment with $CH_2Cl_2/Et_2O$ led to a white residue. Purification by CC ($SiO_2$:$CH_2Cl_2$/MeOH, 19:1) afforded compound (30) as white residue (100 mg, 60%).

In alternative:

In an inert atmosphere of Argon, compound (29) (0.105 mmol), (L)-Fmoc-Ala-OH (49 mg, 0.157 mmol), and DMAP (2.6 mg, 0.02 mmol) were suspended in $CH_2Cl_2$ (0.2 ml). The resulting white suspension was cooled to 0° C., and EDCI (30 mg, 0.157 mmol) was added. The reaction mixture was stirred at 0° C. for 1 h, and then at r.t. for 2 h. The organic phase was washed with $H_2O$ (2×30 ml), HCl 5% (1×30 ml), brine (2×30 ml), dried ($MgSO_4$), and concentrated in vacuo to afford the target compound (30) as a white foam. Treatment with $CH_2Cl_2/Et_2O$ led to a white foam (67 mg, 63%). The compound (30) was characterized as follows:

$R_f$=0.2 ($CH_2Cl_2$/MeOH, 19:1).

$^1$H-NMR (400 MHz, $CDCl_3$): 7.94-7.91 (m, CH-arom., 2 H), 7.88-7.85 (m, CH-arom., 3 H), 7.77-7.72 (m, CH-arom., 8 H), 7.70-7.61 (m, CH-arom., 10 H), 7.57 (d, J=6.56, CH-arom., 1 H), 7.51 (d, J=7.96, CH-arom., 2 H), 7.36 (t, $J_1$=7.36, $J_2$=7.28, CH-arom., 2 H), 7.29-7.24 (m, CH-arom., 4 H), 6.92 (d, J=8.08, CH-arom., 2 H), 6.76 (d, J=7.36, CH-arom., 1 H), 5.58 (br. s, NH, 2 H), 5.07 (s, $OCH_2$, 2 H), 5.05 (s, $OCH_2$, 2 H), 4.54 (br. q, CH-aliph., 2 H), 4.33 (m, $OCH_2$, 2 H), 4.19 (t, CH-aliph., 1 H), 1.39-1.36 (m, $CH_3$, 6 H).

Dept135 (50 MHz, $CDCl_3$): 135.42 (d, J=1.15, CH-arom., 3 H), 134.64 (d, J=5.30, CH-arom., 2 H), 134.05 (d, J=5.15, CH-arom., 6 H), 130.45 (d, J=6.40, CH-arom., 6 H), 129.68 (s, CH-arom., 2 H), 128.73 (d, J=6.60, CH-arom., 2 H), 127.84 (s, CH-arom., 2 H), 127.38 (s, CH-arom., 1 H), 127.30 (s, CH-arom., 1 H), 126.74 (s, CH-arom., 1 H), 124.86 (s, CH-arom., 2 H), 119.53 (s, CH-arom., 2 H), 114.52 (s, CH-arom., 2 H), 69.00 (s, $OCH_2$, 2 H), 66.61 (s, $OCH_2$, 2 H), 66.45 (s, $OCH_2$, 2 H), 50.17 (s, CH-aliph., 1 H), 48.02 (s, CH-aliph., 1 H), 46.68 (s, CH-aliph., 1 H), 17.55 (s, $CH_3$, 6 H).

$^{13}$C-NMR (50 MHz, $CDCl_3$): 172.16, 171.90, 158.22, 156.17, 147.55, 144.25 (d, J=9.75), 141.63, 137.83, 137.38, 135.42 (d, J=1.15), 134.64 (d, J=5.30), 134.05 (d, J=5.15), 130.45 (d, J=6.40), 129.68, 128.73 (d, J=6.60), 127.84,

30

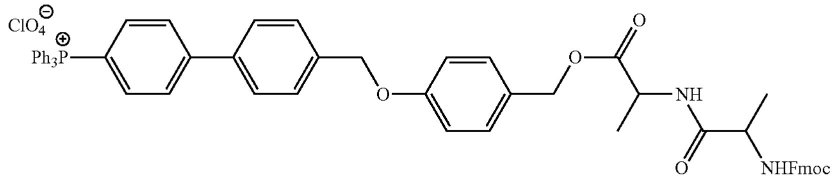

127.61, 127.38, 127.30, 126.74, 124.86, 119.53, 117.70 (d, J=44.55), 116.31 (d, J=45.30), 114.52, 69.00, 66.61, 66.45, 50.17, 48.02, 17.55.

EXAMPLE 15

Phosphonium Supported Amine Scavenger

31

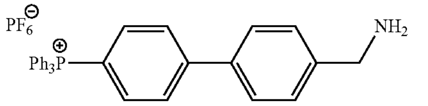

To compound (19) (615 mg, 1 mmol, 1.0 equiv) in $CH_2Cl_2$ (1.5 mL) was added $PPh_3$ (393 mg, 1.5 mmol, 1.5 equiv) $THF/H_2O$ (1.5 mL/0.1 mL). After 1 h the solution was heated to reflux for 3 h. The solution was cooled to room temperature, was diluted with $CH_2Cl_2$ and was dried over anhydrous $Na_2SO_4$ and was concentrated under reduced pressure. The crude product was diluted with $CH_2Cl_2$ (2 ml) and was crunched with $Et_2O$ (10 mL) four times to afford target compound (31) (564 mg, 96%) as a solid foam. The compound (31) was characterized as follows:

$^1$H NMR (400 MHz, $CDCl_3$) 8.18-8.11 (m, 2H), 7.93-7.83 (m, 2H), 7.76-7.71 (m, 6H), 7.68-7.60 (m, 11H), 7.41 (d, J=8.0 Hz, 2H), 3.87 (s, 2H), 1.72 (bs, 2H).

$^{13}$C NMR (100 MHz, $CDCl_3$) 148.1 (d, J=2.9 Hz), 144.4 (s), 136.7 (s), 135.7 (d, J=2.5 Hz), 135.0 (d, J=10.6 Hz), 134.4 (d, J=10.3 Hz), 130.7 (d, J=12.9 Hz), 128.9 (d, J=13.2 Hz), 128.1 (s), 127.7 (s), 117.6 (d, J=89.1 Hz), 115.3 (d, J=91.1 Hz), 45.9 (s).

$^{31}$P (162 MHz, $CDCl_3$) 23.1, −143.9 (sept, J=713 Hz).

IR (film) 1595, 1438, 1108, 827 (P—F) $cm^{-1}$.

EXAMPLE 16

Phosphonium Supported Isocyanate Reagent

32

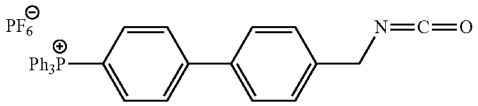

To triphosgene (23.7 mg, 0.08 mmol, 0.4 equiv) in $CH_2Cl_2$ (0.9 mL) at −10° C. was added $NEt_3$ (34 μL, 0.24 mmol, 1.2 equiv). After 5 min a solution of compound (31) (118 mg, 0.2 mmol, 1.0 equiv) in $CH_2Cl_2$ (0.6 mL) was added. The solution was heated to room temperature for 3 h. The was diluted with $CH_2Cl_2$ (20 ml) and was washed with HClaq (5 mL, 1M), with water (5 mL). The organic solution was dried over anhydrous $MgSO_4$ and was concentrated under reduced pressure to afford the target compound (32) (102 mg, 83%) as a solid foam. The compound (32) was characterized as follows:

$^1$H NMR (400 MHz, $CDCl_3$) 8.15-8.10 (m, 2H), 7.87-7.83 (m, 2H), 7.76-7.62 (m, 17H), 7.41 (d, J=7.9 Hz, 2H), 4.53 (s, 2H).

$^{13}$C NMR (100 MHz, $CDCl_3$) 148.0 (d, J=2.8 Hz), 138.4 (s), 138.3 (s), 136.1 (d, J=2.5 Hz), 135.3 (d, J=10.6 Hz), 134.7 (d, J=10.2 Hz), 131.1 (d, J=12.8 Hz), 129.4 (d, J=13.2 Hz), 128.4 (s), 128.0 (s), 123.5 (s), 118.0 (d, J=89.1 Hz), 116.1 (d, J=90.8 Hz), 46.5 (s).

$^{31}$P (162 MHz, $CDCl_3$) 23.1, −143.9 (sept, J=713 Hz).

IR (film) 2923, 2260 (C═N), 1596, 1438, 1108, 827 (P—F) $cm^{-1}$.

EXAMPLE 17

Phosphonium Supported Linkers

33

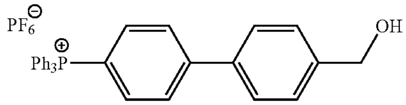

To compound (13) (20.0 g, 37 mmol, 1.0 equiv) in $CH_3CN$ (160 mL) and $H_2O$ (40 ml) was added $KPF_6$ (8.2 g, 44 mmol, 1.2 equiv). After 1 h the mixture was concentrated under reduced pressure and diluted with $CH_2Cl_2$ (250 mL). The resulting mixture was washed with water (75 mL). The aqueous layer was washed with $CH_2Cl_2$ (100 mL). The organic solution was washed two times with water (100 mL), was dried over $MgSO_4$ and concentrated under reduced pressure to give (21.5 g, 99%) of pure target compound (33).

36

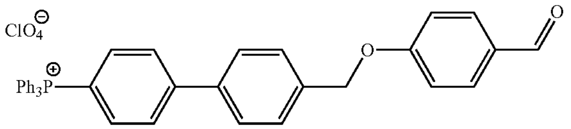

In an inert atmosphere of argon, compound (13) (5 g, 9.17 mmol), 4-hydroxybenzaldehyde (1.68 g, 13.75 mmol), and $PPh_3$ (3.61 g, 13.75 mmol) were dissolved in $CH_2Cl_2$ (100 ml). The resulting reaction mixture was cooled to −15° C., and DEAD (2.1 ml, 13.29 mmol) was slowly added. The obtained pale red solution was then stirred at r.t. for 2 h, and quenched with $H_2O$ (100 ml). The organic phase was separated, washed with brine (2×100 ml), dried ($Na_2SO_4$), and concentrated in vacuo to afford a slightly yellow foam. Treatment with $CH_2Cl_2/Et_2O$ led to a mixture of phosphonium salts.

At r.t., the above mixture of phosphonium salts (6 g, 9.24 mmol) was dissolved in a solution of $CH_2Cl_2$/MeCN (45 ml, 1:3.5), and $LiClO_4$ (1 g, 9.24 mmol) was added. The resulting reaction mixture was stirred for 1 h, and concentrated in vacuo affording a white foam. This white foam was taken up with $CH_2Cl_2$ (50 ml), washed with $H_2O$ (2×50 ml), brine (2×50 ml), and concentrated in vacuo to afford a white foam. Treatment with $CH_2Cl_2/Et_2O$ revealed the desired compound (36) as a white foam (5.6 g, 94%). The compound (36) was characterized as follows:

$^1$H-NMR (400 MHz, $CDCl_3$): 9.80 (s, 1 H), 7.95-7.53 (m, 25 H), 7.06 (d, J=8.5 Hz, 2 H), 5.18 (s, 2 H).

$^{13}$C-NMR (50 MHz, $CDCl_3$): 191.36, 163.98, 148.11, 138.09, 136.16 (d, J=2.6 Hz), 135.42 (d, J=10.7 Hz), 134.81 (d, J=10.3 Hz), 132.49, 131.19 (d, J=12.9 Hz), 130.49, 129.91, 129.50 (d, J=13.2 Hz), 128.70, 128.28, 117.97 (d, J=89.1 Hz), 116.08 (d, J=90.1 Hz), 70.11.

$^{31}$P-NMR (162 MHz, $CDCl_3$): 24.1.

37

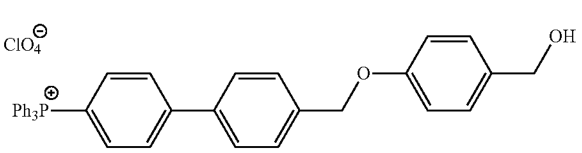

In an inert atmosphere of Argon, compound (36) (5 g, 7.70 mmol) was dissolved in $CH_2Cl_2$ (30 ml), and cooled to −78° C. $NaBH_4$ (350 mg, 9.24 mmol), dissolved in EtOH (10 ml) was then added, and the resulting reaction mixture warmed to 0° C. After 1.5 h, the reaction vessel was quenched with a sat. aq. soln. of $NH_4Cl$ (50 ml), and extracted with $CH_2Cl_2$ (2×50 ml). The organics were washed with $H_2O$ (2×100 ml), brine (2×100 ml), dried ($Na_2SO_4$), and concentrated in vacuo to afford a slightly yellow foam. Purification by CC ($SiO_2$: $CH_2Cl_2$/MeOH, 19:1) afforded the desired compound (37) as a white foam (2.5 g, 50%). The compound (37) was characterized as follows:

$^{13}$C-NMR (100 MHz, $CDCl_3$): 158.19, 148.13, 138.68, 138.16, 136.15 (d, J=2.4 Hz), 135.40 (d, J=10.6 Hz), 134.79 (d, J=10.3 Hz), 134.50, 131.18 (d, J=12.8 Hz), 129.43 (d, J=13.2 Hz), 129.04, 128.57, 128.12, 117.95 (d, J=89.1 Hz), 115.52 (d, J=90.7 Hz), 69.79, 64.78.

$^{31}$P-NMR (162 MHz, $CDCl_3$): 24.1.

38

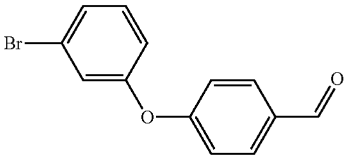

In an inert atmosphere of Argon, 3-bromophenol (17.3 g, 100 mmol), 4-fluorobenzaldehyde (10.6 ml, 100 mmol), and $K_2CO_3$ (powder) (16.6 g, 120 mmol) were suspended in N,N-dimethylacetamide (100 ml). The resulting suspension was refluxed (170° C.) for 14 h, cooled to r.t., quenched with $H_2O$ (150 ml), and extracted with $CHCl_3$ (2×100 ml). The organics were washed with $H_2O$ (2×200 ml), brine (2×200 ml), dried ($Na_2SO_4$), and concentrated in vacuo to afford a deep brown oil. Extraction with hexane (1 l), led to compound (38) as a yellow oil which was pure enough to continue (22 g, 79%). N.B.: Still the presence of N,N-dimethylacetamide. The compound (38) was characterized as follows:

$^{1}$H-NMR (400 MHz, $CDCl_3$): 9.89 (s, 1 H), 7.83 (d, J=8.8 Hz, 2 H), 7.29-7.19 (m, 3 H), 7.05-6.95 (m, 3 H).

$^{13}$C-NMR (100 MHz, $CDCl_3$): 191.05, 162.65, 156.44, 132.38, 132.18, 131.61, 128.28, 123.80, 123.47, 119, 21, 118.42.

39

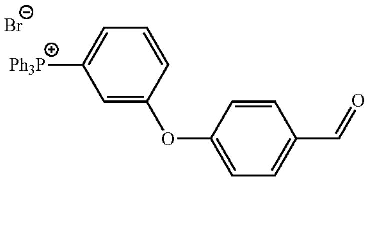

In an inert atmosphere of Argon (high flow), compound (38) (10 g, 36 mmol), $PPh_3$ (14.16 g, 54 mmol), and $NiBr_2$ (3.93 g, 18 mmol) were suspended in PhCN (360 ml). The resulting green solution was refluxed (200° C.) for 12 h, cooled to r.t., and quenched with a 10% aq. soln. of KBr (300 ml). The layers were separated, the aq. phase extracted with $CH_2Cl_2$ (2×100 ml), and the combined organic layers were concentrated in vacuo to afford a brown oil. This oil was taken up (in a 1 l flask) with hexane (500 ml), and rotated vigorously in order that the crude compound glues on the faces of the flask. The hexane phase was decanted revealing a thick brown oil. Treatment with $CH_2Cl_2$/$Et_2O$ afforded compound (39) as a white foam (13 g, 70%). N.B.: Still the presence of N,N,-dimethylacetamide. The compound (39) was characterized as follows:

$^{1}$H-NMR (300 MHz, $CDCl_3$): 9.86 (s, 1 H), 7.89-7.81 (m, 5 H), 7.77-7.73 (m, 7 H), 7.61-7.54 (m, 7 H), 7.43-7.36 (m, 2 H), 7.10 (d, J=7.6 Hz, 2 H).

$^{31}$P-NMR (122 MHz, $CDCl_3$): 24.1.

40

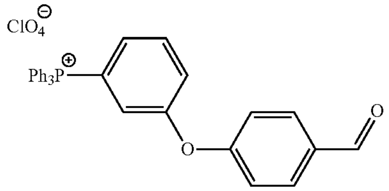

At r.t., compound (39) (12 g, 22.2 mmol) was dissolved in a solution of $CH_2Cl_2$/MeCN (110 ml, 1:3.4), and $LiClO_4$ (4.73 g, 44.4 mmol) was added. The resulting reaction mixture was stirred for 2 h, and concentrated in vacuo affording a brown foam. This foam was taken up with $CH_2Cl_2$ (100 ml), washed with $H_2O$ (2×100 ml), brine (2×100 ml), dried ($Na_2SO_4$), and concentrated in vacuo to afford a brown foam. Treatment with $CH_2Cl_2$/$Et_2O$ revealed the target compound (40) as a white (pale brown) foam (11.5 g, 93%).

$^{1}$H-NMR (300 MHz, $CDCl_3$): 9.86 (s, 1H), 7.91-7.55 (m, 19 H), 7.47-7.38 (m, 2 H), 7.15-7.08 (m, 2 H).

$^{31}$P-NMR (122 MHz, $CDCl_3$): 24.2.

41

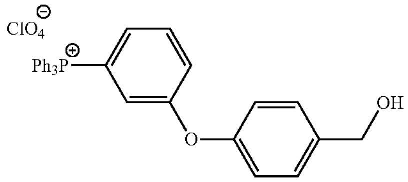

In an inert atmosphere of Argon, compound (40) (10.5 g, 18.78 mmol) was dissolved in $CH_2Cl_2$ (70 ml), and cooled to −78° C. $NaBH_4$ (852 mg, 22.53 mmol), dissolved in EtOH (20 ml) was then added, and the resulting reaction mixture warmed to 0° C. After 2 h, the reaction vessel was quenched with a sat. aq. soln. of $NH_4Cl$ (100 ml), and extracted with $CH_2Cl_2$ (2×100 ml). The organics were washed with $H_2O$ (2×200 ml), brine (2×200 ml), dried ($Na_2SO_4$), and concentrated in vacuo to afford a white (slightly yellow) foam. Treatment with $CH_2Cl_2$/$Et_2O$ led to the target compound (41) as a white foam (9.10 g, 86%). The compound (41) was characterized as follows:

$^{1}H$-NMR (300 MHz, $CDCl_3$): 7.86-7.81 (m, 3 H), 7.77-7.52 (m, 14 H), 7.32-7.20 (m, 3 H), 6.98-6.89 (m, 3 H), 4.60 (s, 2 H), 3.43 (bs, 1 H).

$^{31}P$-NMR (122 MHz, $CDCl_3$): 24.1.

34

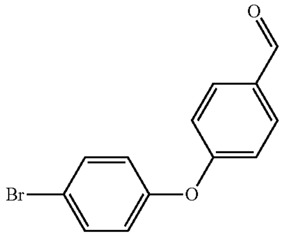

Compound (34) was prepared by coupling between 4-bromophenol and 4-fluorobenzaldehyde (see formation of 38). The compound (34) was characterized as follows:

M.p. 50-52° C.

$^{1}H$ NMR (400 MHz, $CDCl_3$) δ 9.90 (s, 1H), 7.84-7.82 (m, 2H), 7.49-7.47 (m, 2H), 7.02-7.04 (m, 2H), 6.96-6.94 (m, 2H).

$^{13}C$ NMR (100 MHz, $CDCl_3$) 190.7, 166.7, 158.1, 133.2, 132.1, 131.7, 122.1, 117.9, 117.7.

IR (film) 3059, 1893, 1686 (C═O), 1574, 1479, 1227, 1009 $cm^{-1}$.

LRMS (APCI, Pos) calcd for $C_{13}H_9{}^{79}Br_1O_2$ $[M+H]^+$: 277.0 m/z, observed 276.9; calcd for $C_{13}H_9{}^{81}Br_1O_2$ $[M+H]^+$: 279.0 m/z, observed 278.9.

35

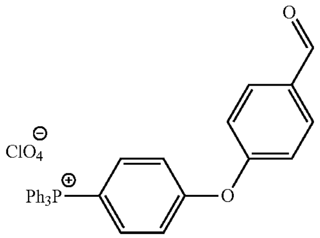

Compound (35) was prepared from compound (34) (see formation of 39).

42

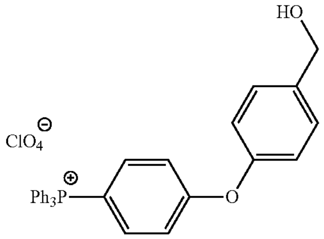

Compound (42) was prepared by reducing compound (35) according to the same method as described for compound (41). Compound (42) was characterized as follows:

43

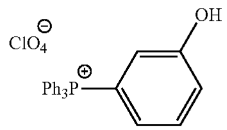

Compound (43) was prepared from 4-bromophenol and triphenylphosphine (see the synthesis of (39)) Compound (42) was characterized as follows:

LRMS (APCI, Pos) calcd for $C_{24}H_{20}OP_1$ $[M]^+$: 355.1 m/z, observed 355.0. LRMS (APCI, Neg) calcd for $^{35}ClO_4$ $[M]^-$: 99.0 m/z, observed 99.1; $^{37}ClO_4$ $[M]^-$: 101.0 m/z, observed 101.0.

44

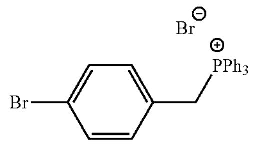

4-Bromobenzyl bromide (50 g, 200 mmol, 1.0 equiv), triphenylphosphine (57 g, 220 mmol, 1.1 equiv), in $CHCl_3$ (400 mL, 0.5 M) was heated under reflux 4 h. The solution was cooled to room temperature and the phosphonium was crunched with $Et_2O$ (1.5 L). The crude product was diluted with $CH_2Cl_2$ (300 mL) and was crunched with $Et_2O$ (1.5 L) was filtered under Buchner and washed with $Et_2O$ (500 mL) to afford target compound (44) as a white solid (123 g, quant. yield).

45

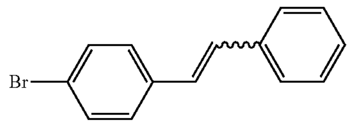

To compound (44) (100 g, ca 167 mmol) suspended in THF (330 mL, 0.5 M) was added KH (9.5 g, 236 mmol, 1.4 equiv) after 1 h the mixture was cooled to 0° C. Benzaldehyde (28.0 mL, 276 mmol, 1.67 equiv) was added and the mixture was warmed to rt for 18 h. A saturated NH4Cl aqueous solution (50 mL) was carefully added and the mixture was filtered under Buchner. The filtrate was washed with CH2Cl2 (1.0 L). The organic phase was washed with water (500 mL) and dry under MgSO4. After a flash chromatography (Hexane/$CH_2Cl_2$, 0:100 and 20:90) the mixture of isomers (E/Z=1:0.6) (45) was obtained as a white solid (41.0 g, 95%).

46

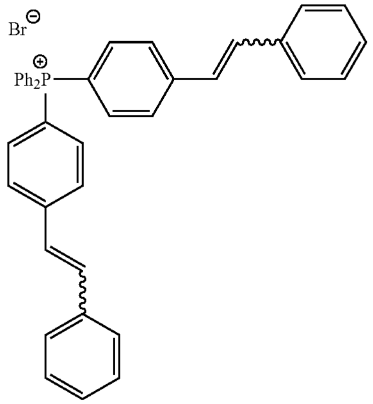

To compound (45) (3.7 g, 14 mmol, 1.0 equiv) in THF (45 mL, 0.3 M) at −78° C. was added n-BuLi (1.6 M in Hexane) (9.2 mL, 14.7 mmol, 1.05 equiv). After 45 min $Ph_2PCl$ (2.7 mL, 14.7 mmol, 1.05 equiv) was added. After 15 min the solution was warmed to 0° C. for 30 min and was filtrated on silica gel rinse with $Et_2O$ concentrated in vacuo. To this crude phosphine (ca 14 mmol, 1.0 equiv), and compound (45) (3.7 g, 14 mmol, 1.0 equiv) in benzonitrile (50 mL, 0.28 M) was added $NiBr_2$ (1.5 g, 7.0 mmol, 0.5 equiv). The mixture was heated to reflux for 3 h. The solution was cooled to room temperature and a 10% (w/w) KBr aqueous solution (25 mL) was added. The layers were separated, and the aqueous layer was washed two times with $CH_2Cl_2$ (50 mL). The organic solution was washed three times with water (25 mL), was dried over anhydrous $MgSO_4$, filtered concentrated under reduced pressure. To the resulting solution was added hexane (250 mL) to precipitate the crude product. The crude product was diluted with $CH_2Cl_2$ (20 ml) and was crunched with Et2O (100 mL). This operation was repeated two times to afford (46) as a white solid (4.5 g, 52%).

47

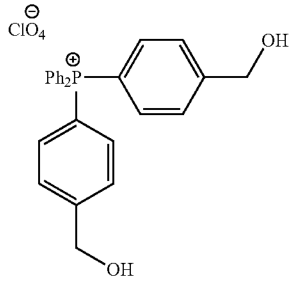

To compound (46) (3.4 g, 5.3 mmol, 1.0 equiv) in CH3CN (20 mL, 0.27 M) was added $LiClO_4$.3H20 (1.3 g, 7.9 mmol, 1.5 equiv). After 1 h the mixture was concentrated under reduced pressure and diluted with $CH_2Cl_2$ (50 mL). The resulting mixture was washed with water (25 mL). The aqueous layer was washed with $CH_2Cl_2$ (25 mL). The organic solution was washed two times with water (10 mL), was dried over $MgSO_4$ and concentrated under reduced pressure. Compound (46) (ca 5.3 mmol, 1.0 equiv) was dilute in $CH_2Cl_2$ (40 mL) and MeOH (10 mL). The resulting solution was cooled to −78° C. and $O_3$ was passed to sature the media then the solution and was purged with $O_2$ and Argon. $NaBH_4$ (420 mg, 14 mmol, 2.5 equiv) was added to the solution. After 30 min the solution was warmed to 0° C. for 1 h. A half saturated NH4Cl aqueous solution (10 mL) was carefully added. The layers were separated and the aqueous layer was washed two times with $CH_2Cl_2$ (10 mL). The organic solution was washed three times with water (10 mL) was dried over $MgSO_4$ and was concentrated under reduced pressure. The crude product was diluted with $CH_2Cl_2$ (6 mL) and was crunched with $Et_2O$ (25 mL) to afford pure compound (47) as a white solid (1.8 g, 78%). Compound (47) was characterized as follows:

$^1H$ NMR (400 MHz, $CDCl_3$/MeOH) 7.85-7.40 (m, 18H), 4.76 (s, 4H), 2.70 (bs, 2H)

$^{13}C$ NMR (100 MHz, $CDCl_3$/MeOH) 151.5 (d, J=2.6 Hz), 135.6 (d, J=2.6 Hz), 134.5 (d, J=7.7 Hz), 134.4 (d, J=6.1 Hz), 130.6 (d, J=14.4 Hz), 128.6 (d, J=15.1 Hz), 118.4 (d, J=89.1 Hz), 115.1 (d, J=91.0 Hz), 63.2 (s).

$^{31}P$ (162 MHz, $CD_2Cl_2$) 22.7.

LRMS (APCI, Pos) calcd for $C_{26}H_{24}O_2P_1$ $[M]^+$: 399.2 m/z, observed 399.0.

LRMS (APCI, Neg) calcd for $^{35}ClO_4$ $[M]^-$: 99.0 m/z, observed 99.0; $^{37}ClO_4$ $[M]^-$: 101.0 m/z, observed 101.1.

EXAMPLE 18

Phosphonium Supported Amine Reagent

48

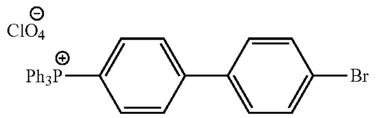

In an inert atmosphere of argon (with a high flow), 4,4'-dibromobiphenyl (749 mg, 2.4 mmol, 2.0 equiv), $PPh_3$ (317 mg, 1.2 mmol, 1 equiv), and dry $NiBr_2$ (132 mg, 0.60 mmol, 0.5 equiv) were suspended in PhCN (6.7 mL, 0.3 M). The resulting green reaction mixture was stirred at 200° C. for 2 h, and then cooled to r.t. The deep green reaction vessel was quenched with a 10% aq. soln. of KBr (10 ml), and extracted with $CH_2Cl_2$ (2×7 ml). The combined organic phases were washed with $H_2O$ (2×5 ml), dried ($MgSO_4$), and concentrated in vacuo to afford a brown oil. The resulting brown oil was taken up (in a flask) with hexane (65 ml), and the crude product glued on the faces of the flask as a thick oil. The hexane layer was separated, and this operation was carried out twice. The resulting thick oil was taken up with $CH_2Cl_2$ (2 mL), and $Et_2O$ (20 ml) was added in order to precipitate the phosphonium salt. The flask was rotated vigorously, and the organic phase was decanted. This operation was done twice, affording the desired compound (48) as a yellow residue, which was pure enough to continue (427 mg, 59%), has been characterized has follows:

$^1H$ NMR (400 MHz, $CDCl_3$) δ 7.80-7.75 (m, 2H), 7.75-7.12 (m, 19H), 7.10 (d, J=7.8 Hz, 2H). $^{13}C$ NMR (100 MHz, $CDCl_3$) δ 146.4 (s), 137.6 (s), 135.4 (d, J=2.5 Hz), 134.6 (d, J=10.7 Hz), 133.8 (d, J=10.2 Hz), 131.8 (s), 130.5 (d, J=12.8 Hz), 128.9 (s), 128.6 (d, J=13.3 Hz), 123.1 (s), 116.8 (d, J=90.8 Hz), 115.4 (d, J=89.0 Hz).

49

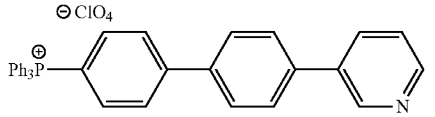

In a 25 mL flask, (48) (594 mg, 1.0 mmol, 1 equiv) was dissolved in 1,2-dichloroethane (2.5 mL) and dioxane (5 mL). Then, 3-Pyridylboronic acid (synthesis: Danheiser, R. L. *Organic Synthesis,* 81, 89-97) (210 mg, 0.54 mmol, 0.54 equiv) and a $Na_2CO_3$ aqueous solution (3.7 ml, 2 M, 7.4 equiv) were added. The solution was reflux for 30 minutes under argon and then cooled to room temperature. $Pd(OAc)_2$ (2.2 mg, 0.01 mmol, 0.01 equiv) and $(o\text{-tolyl})_3P$ (12.5 mg 0.04 mmol, 0.04 equiv) were dissolved in degassed dioxane (1 mL) and transfer to the reaction flask. The solution was reflux for 2 hours under argon. The solution was cooled to room temperature, was diluted with $CH_2Cl_2$ (40 mL) and washed with a satured $NaHCO_3$ aqueous solution (5 ml). The organic layer was dried over anhydrous $MgSO_4$, filtered and concentrated. The product was purified by filtration on a small pad of silica gel ($MeOH/CH_2Cl_2$ 3:97) to afford the target compound (49) (461 mg, 78%) as a solid foam. Compound (49) was characterized as follows:

$^1H$ NMR (400 MHz, $CDCl_3$) δ 8.83 (s, 1H), 8.56 (s, 1H), 8.01-7.99 (m, 2H), 7.86-7.78 (m, 4H), 7.76-7.69 (m, 18H), 7.41 (m, 1H).

$^{13}C$ NMR (100 MHz, $CDCl_3$) δ 149.0 (s), 148.3 (s), 147.6 (s), 138.7 (s), 138.0 (s), 135.9 (s), 135.7 (s), 135.2 (d, J=10 Hz), 134.6 (d, J=10 Hz) 130.9 (d, J=13 Hz), 129.2 (d, J=13 Hz), 128.4 (s), 128.1 (s), 123.9 (s), 117.8 (d, J=89 Hz), 115.9 (d, J=91 Hz).

$^{31}P$ (162 MHz, $CDCl_3$) δ 22.8.

EXAMPLE 19

Phosphonium Supported Oxidizing Reagent

50

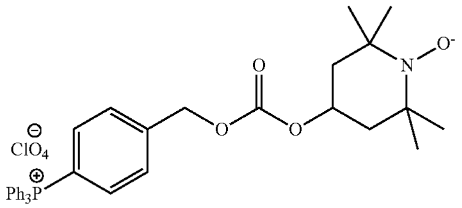

To a 25 mL flask, Triphosgene (178 mg, 0.6 mmol, 0.6 equiv) was dissolved in $CH_2Cl_2$ (2.0 mL) and cooled to −20° C. and Pyridine (162 μL, 2.0 mmol, 2 equiv) was added dropwise. OH-TEMPO (345 mg, 2.0 mmol, 2.0 equiv) was dissolved in $CH_2Cl_2$ (1 mL) and slowly transfer to the reaction flask. After 15 min the solution was stirred at room temperature for 30 min. (7) (467 mg, 1.0 mmol, 1 equiv) and Pyridine (324 μL, 4 mmol, 4 equiv) were added and the solution was stirred for 3 h. The solution was diluted with $CH_2Cl_2$ (40 mL) and washed with $H_2O$ (10 ml). The organic layer was dried over anhydrous $MgSO_4$, filtered, concentrated and was crunched with $Et_2O$ (30 ml) four times to afford pure compound (50) (595 mg, 90%) as a solid foam. Treatment of compound (50) by phenylhydrazine afforded compound (51):

51

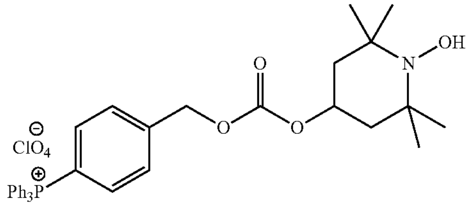

$^1H$ NMR (400 MHz, $CDCl_3$) δ 7.87-785 (m, 3H), 7.74-7.63 (m, 8H), 7.61-7.57 (m, 8H), 5.27 (s, 2H), 4.90 (m, 1H), 1.99 (d, J=11.5 Hz, 2H), 1.63 (t, J=11.5 Hz, 2 H), 1.21 (s, 6H), 1.18 (s, 6 H).

$^{13}C$ NMR (100 MHz, $CDCl_3$) δ 153.4 (s), 143.0 (s), 135.1 (s), 134.0 (d, J=10 Hz), 133.6 (d, J=10.2 Hz), 130.1 (d, J=12.8 Hz), 128.7 (d, J=13 Hz), 116.5 (d, J=91 Hz), 116.4 (d, J=89 Hz), 70.3 (s), 67.1 (s), 59.8 (s), 42.4 (s), 30.5 (s), 19.8 (s).

EXAMPLE 20

Phosphonium Supported Spiro Compound

52

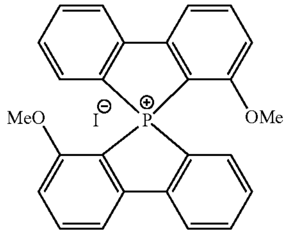

To 2,2'-diiodo-3-methoxybiphenyl (335 mg, 0.77 mmol, 2.0 equiv) in Et2O (4 mL) at −78° C., was added n-BuLi (1.1 mL, 1.54 mmol, 1.4 M in hexane, 4.0 equiv). After 15 min the solution was warmed to 0° C. for 15 min and to room temperature for 30 min. Triphenyl phosphate (125 mg, 0.385 mmol, 1.0 equiv) in $Et_2O$ (0.5 mL) was added to the solution and after 15 min the resulting mixture was refluxed for 8 h. The mixture was cooled to room temperature concentrated in vacuo, diluted with $CH_2Cl_2$ (2 mL) and cooled to 0° C. HI (0.6 mL, 57% in water) was added and the solution was warmed to room temperature for 15 min. $CH_2Cl_2$ (25 mL) and water (5 mL) were added. The organic phase was washed with a saturated NaHCO3 aqueous solution (5 mL) dry under $MgSO_4$ and concentrated in vacuo. The residue was purified by flash chromatography ($MeOH/CH_2Cl_2$, 0:100-5:95) to afford pure compound (52) (157 mg, 78%) as a solid foam. Compound (52) was characterized as follows:

$^1H$ NMR (400 MHz, $CDCl_3$) 8.17 (dd, $J_{H\text{-}H}$=7.7 Hz, $J_{P\text{-}H}$=3.2 Hz, 2H), 7.90 (t, $J_{H\text{-}H}$=7.7 Hz, 2H), 7.91-7.84 (m, 2H), 7.77 (dd, $J_{H\text{-}H}$=7.6 Hz, $J_{P\text{-}H}$=2.9 Hz, 2H), 7.51 (td, $J_{H\text{-}H}$=7.5 Hz, $J_{P\text{-}H}$=4.7 Hz, 2H), 7.41 (dd, $J_{P\text{-}H}$=11.5 Hz, $J_{H\text{-}H}$=7.5 Hz, 2H), 7.06 (t, H=7.5 Hz, 2H), 3.62 (s, 6H).

$^{13}C$ NMR (100 MHz, $CDCl_3$) 162.9 (d, J=4.1 Hz), 147.1 (d, J=18.9 Hz), 145.5 (d, J=21.7 Hz), 140.6 (d, J=1.2 Hz), 136.7 (d, J=2.0 Hz), 131.2 (d, J=12.7 Hz), 131.0 (d, J=12.5

Hz), 124.3 (d, J=10.6 Hz), 117.4 (d, J=94.5 Hz), 116.4 (d, J=10.5 Hz), 113.7 (d, J=6.9 Hz), 101.7 (d, J=98.8 Hz), 53.6 (s).

EXAMPLE 21

Phosphonium Supported Oxidizing Reagent

53

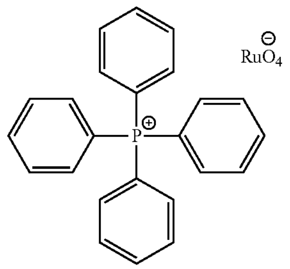

$PPh_4RuO_4$ was synthesised according a procedure related in *Inorg. Chem.* 1993, 32, 268-271.

Oxidation of Cinnamyl Alcohol by $PPh_4RuO_4$\NMO System

The oxidation was executed according the procedure related in *J. Chem. Soc., Chem, Comm.* 1987, 1625-1627.

To a 10 mL flask, cinnamyl alcohol (67 mg, 0.5 mmol, 1 equiv) was dissolved, under argon, in $CH_2Cl_2$ (2.5 mL, 0.2M) containing both the 4 Å sieves and N-methyl morpholine N-oxide (NMO) (88 mg, 0.75 mmol, 1.5 equiv). After stirring the solution for 10 min, $PPh_4RuO_4$ (12.5 mg, 0.025 mmol, 0.05 equiv) was added and the solution was stirred overnight. The solution was diluted with $CH_2Cl_2$ (40 mL) and washed with a saturated aqueous $Na_2SO_3$ solution (10 ml), brine (10 ml) and a saturated $CuSO_4$ aqueous solution. The organic layer was dried over anhydrous $MgSO_4$, filtered on celite, concentrated. The phosphonium was crunched with $Et_2O$ (20 ml) to afford a $PPh_4RuO_4$ precipitate (9.7 mg). The $Et_2O$ layer was evaporated to afford the cinnamaldehyde (54 mg, 81%). The $PPh_4RuO_4$ precipitate (9.7 mg) was reused in the same condition to afford the cinnamaldehyde (49 mg, 73%).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for using a compound of formula (I):

(I)

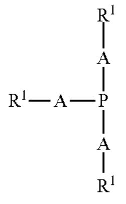

wherein

A is selected from the group consisting of furyl, phenyl, pyridyl, naphthyl, and thiophenyl; and $R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl comprising the step of attaching a molecule to the phosphorus atom of said compound of formula (I) so as to control the solubility of said molecule.

2. A method for using a compound of formula (I):

(I)

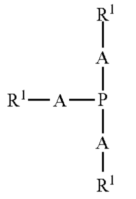

wherein

A is selected from the group consisting of furyl, phenyl, pyridyl, naphthyl, and thiophenyl; and $R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl comprising:

attaching a molecule to the phosphorus atom of said compound of formula (I) or to a linker attached to the phosphorus atom of said compound of formula (I) so as to control the solubility of said molecule;

solubilizing said compound of formula (I) having said molecule attached to the phosphorus atom or having said molecule attached to said linker attached to the phosphorus atom in conditions suitable for solubilizing said compound of formula (I) having said molecule attached to the phosphorus atom or said molecule attached to said linker attached to the phosphorus atom; and precipitating said compound of formula (I) having said molecule attached to the phosphorus atom or having said molecule attached to said linker attached to the phosphorus atom in conditions suitable for precipitating said compound of formula (I) having said molecule attached to the phosphorus atom or said molecule attached to said linker attached to the phosphorus atom.

3. The method of claim 2, wherein said molecule has a molecular weight ranging from 40 to 1200 g/mol.

4. The method of claim 2, wherein said molecule has a molecular weight ranging from 60 to 700 g/mol.

5. The method of claim 2, wherein said conditions suitable for solubilizing said compound of formula (I) having said molecule attached to the phosphorus atom or said molecule attached to said linker attached to the phosphorus atom comprise at least one solvent chosen from dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile, acetone, methanol, 2-propanol, ethyl acetate and nitrobenzene.

6. The method of claims 5, wherein said compound of formula (I) having said molecule attached to the phosphorus atom or said molecule attached to said linker attached to the phosphorus atom is solubilized in a first solvent chosen from dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile, nitrobenzene, and mixtures thereof.

7. The method of claim 6, wherein said conditions suitable for precipitating said compound of formula (I) having said molecule attached to the phosphorus atom or said molecule attached to said linker attached to the phosphorus atom comprise at least one solvent chosen from diethylether ($Et_2O$), tetrahydrofuran (THF), hexanes, toluene, benzene, chlorobenzene, tetrachloromethane, water and t-butyl methyl ether.

8. The method of claim 6, wherein said compound of formula (I) having said molecule attached to the phosphorus atom or said molecule attached to said linker attached to the phosphorus atom is precipitated in the presence of a second solvent chosen from diethylether ($Et_2O$), tetrahydrofuran (THF), hexanes, toluene, benzene, chlorobenzene, tetrachloromethane and t-butyl methyl ether.

9. The method of claim 8, wherein said compound of formula (I) having said molecule attached to the phosphorus atom or said molecule attached to said linker attached to the phosphorus atom precipitates by adding said second solvent to a solution comprising said compound of formula (I) having said molecule attached to the phosphorus atom or said molecule attached to said linker attached to the phosphorus atom substantially solubilized in said first solvent.

10. The method of claim 2, wherein said molecule is attached to the phosphorus atom of said compound of formula (I).

11. The method of claim 2, wherein said molecule is attached to said linker attached to the phosphorus atom of said compound of formula (I).

12. The method of claim 11, wherein said linker is

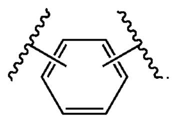

13. The method of claim 2, wherein said molecule is chosen from an amine reagent, a catalyst, a ligand, a chiral ligand, a linker, a coupling reagent, an organic substrate, a phosphine reagent, a tin reagent, a silicon reagent, and a scavenger.

14. The method of claim 2, wherein A is phenyl and $R^1$ is H.

15. The method of claim 2, wherein said method comprises chemically modifying said compound of formula (I) having said molecule attached to the phosphorus atom or said molecule attached to said linker attached to the phosphorus atom.

16. A method for carrying out a chemical reaction comprising:

solubilizing a compound of formula (I):

(I)

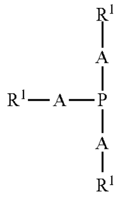

wherein

A is selected from the group consisting of furyl, phenyl, pyridyl, naphthyl, and thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

having a substrate attached to the phosphorus atom or having a substrate attached to a linker attached to the phosphorus atom, in conditions suitable for solubilizing said compound of formula (I) having said substrate attached to the phosphorus atom or said substrate attached to said linker attached to the phosphorus atom and obtaining a solution;

chemically modifying said substrate;

precipitating said compound of formula (I) having said modified substrate attached to the phosphorus atom or having said modified substrate attached to said linker attached to the phosphorus atom in conditions suitable for precipitating said compound of formula (I) having said modified substrate attached to the phosphorus atom or said modified substrate attached to said linker attached to the phosphorus atom, so as to obtain a precipitate in said solution; and separating said precipitate from said solution.

17. A method for carrying out a chemical reaction comprising:

solubilizing a compound of formula (I):

(I)

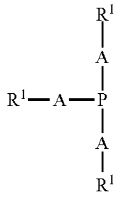

wherein

A is selected from the group consisting of furyl, phenyl, pyridyl, naphthyl, and thiophenyl;

$R^1$ is selected from the group consisting of a hydrogen atom, a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_2$-$C_8$ alkenyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl;

having a substrate attached to the phosphorus atom or having a substrate attached to a linker attached to the phosphorus atom, in solvent conditions comprising at least one solvent chosen from dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile, acetone, methanol, 2-propanol, ethyl acetate and nitrobenzene, so as to obtain a solution;

chemically modifying said substrate;

adding at least one other solvent chosen from diethylether ($Et_2O$), tetrahydrofuran (THF), hexanes, toluene, benzene, chlorobenzene, tetrachloromethane, water and t-butyl methyl ether to said solution so as to cause said compound of formula (I) having said modified substrate attached to the phosphorus atom or having said modified substrate attached to said linker attached to the phosphorus atom to precipitate; and separating said precipitate from said solution.

18. The method of claim 17, wherein said at least one solvent is chosen from dichloromethane ($CH_2Cl_2$), 1,2-dichloroethane ($ClCH_2CH_2Cl$), chloroform, acetonitrile, dimethylformamide (DMF), dimethylsulfoxide (DMSO), benzonitrile, nitrobenzene, and mixtures thereof, and said at least one other solvent is chosen diethylether ($Et_2O$), tetrahydrofuran (THF), hexanes, toluene, benzene, chlorobenzene, tetrachloromethane and t-butyl methyl ether.

19. The method of claim 18, wherein A is phenyl and $R^1$ is H.

* * * * *